US009554708B2

(12) United States Patent
Lee

(10) Patent No.: US 9,554,708 B2
(45) Date of Patent: *Jan. 31, 2017

(54) CATHETER WITH OMNI-DIRECTIONAL OPTICAL TIP HAVING ISOLATED OPTICAL PATHS

(71) Applicant: BIOSENSE WEBSTER, INC., Diamond Bar, CA (US)

(72) Inventor: James K. Lee, San Mateo, CA (US)

(73) Assignee: Biosense Webster, Inc., Diamond Bar, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/666,203

(22) Filed: Mar. 23, 2015

(65) Prior Publication Data
US 2015/0190057 A1    Jul. 9, 2015

Related U.S. Application Data

(63) Continuation of application No. 11/601,065, filed on Nov. 17, 2006, now Pat. No. 8,986,298.

(51) Int. Cl.
*A61B 18/14* (2006.01)
*A61B 5/00* (2006.01)
(Continued)

(52) U.S. Cl.
CPC .......... *A61B 5/0075* (2013.01); *A61B 5/0084* (2013.01); *A61B 5/01* (2013.01); *A61B 5/065* (2013.01);
(Continued)

(58) Field of Classification Search
CPC ..... A61B 18/12; A61B 18/1492; A61B 18/21; A61B 2018/00065; A61B 2018/000636; A61B 2018/00166; A61B 2018/00773; A61B 2018/208; A61B 2018/225; A61B 2018/2261; A61B 5/0075; A61B 5/0074
See application file for complete search history.

(56) References Cited

U.S. PATENT DOCUMENTS 1,791,794 A  2/1931  Chesney
4,469,098 A  9/1984  Davi
(Continued)

FOREIGN PATENT DOCUMENTS

EP  0 195 375 A2  9/1986
EP  0 441 040 A2  8/1991
(Continued)

OTHER PUBLICATIONS

India Patent Office action dated Nov. 27, 2015 issued in application No. IN 1550/KOL/2007, 2 pages.
(Continued)

*Primary Examiner* — Ronald Hupczey, Jr.
(74) *Attorney, Agent, or Firm* — Lewis Roca Rothgerber Christie LLP

(57) ABSTRACT

A catheter enables real-time light measurements, for example, without limitation, diffuse reflectance, fluorescence, etc., from biological materials, such as tissue (including blood), while performing RF ablation. The catheter tip design isolates illumination and collection paths within the tip electrode such that light for illuminating the tissue of interest (e.g., cardiac tissue or blood) is isolated within the tip electrode from light that returns from the tissue to the catheter tip, and vice versa. Such a design advantageously avoids saturation of the optical detector, and ensures diffusion of the illumination light within the medium of interest. The catheter has a catheter body and a tip electrode with a shell wall and a hollow cavity. The shell wall has at least an illumination opening and a collection opening. The catheter further includes a first fiber optic cable in communication with the illumination opening, and a second fiber optic cable (Continued)

in communication with the hollow cavity, wherein light emitted from the first fiber optic cable exits the tip electrode to reach tissue through the illumination opening in defining a first path and returns to the tip electrode from the tissue into the hollow cavity through the collection opening in defining a second path, the first and second paths being optically isolated from each other within the tip electrode. The invention also includes a method of making an ablation electrode tip defining isolated optical paths with in the tip electrode for light exiting the tip electrode and light returning to the tip electrode.

36 Claims, 14 Drawing Sheets

(51) Int. Cl.
  A61B 5/01 (2006.01)
  A61B 5/06 (2006.01)
  A61B 18/00 (2006.01)
  A61B 17/00 (2006.01)

(52) U.S. Cl.
  CPC .. A61B 18/1492 (2013.01); A61B 2017/00057 (2013.01); A61B 2017/00084 (2013.01); A61B 2018/00791 (2013.01); A61B 2018/00982 (2013.01); A61B 2034/2051 (2016.02); A61B 2090/397 (2016.02); A61B 2218/002 (2013.01); A61B 2562/12 (2013.01); Y10T 29/49002 (2015.01)

(56) References Cited

U.S. PATENT DOCUMENTS

| | | |
|---|---|---|
| 4,587,972 A | 5/1986 | Morantte, Jr. |
| 4,669,098 A | 5/1987 | Boatwright |
| 4,669,467 A | 6/1987 | Willett et al. |
| 4,672,961 A | 6/1987 | Davies |
| 4,736,743 A | 4/1988 | Daikuzono |
| 4,819,632 A | 4/1989 | Davies |
| 4,860,743 A | 8/1989 | Abela |
| 5,041,109 A | 8/1991 | Abela |
| 5,061,265 A | 10/1991 | Abela et al. |
| 5,147,348 A | 9/1992 | Leckrone et al. |
| 5,151,096 A * | 9/1992 | Khoury ............... A61N 5/0601 606/15 |
| 5,248,311 A | 9/1993 | Black et al. |
| 5,267,996 A | 12/1993 | Fletcher |
| 5,370,608 A | 12/1994 | Sahota et al. |
| 5,370,640 A | 12/1994 | Kolff |
| 5,391,199 A | 2/1995 | Ben-Haim |
| 5,443,489 A | 8/1995 | Ben-Haim |
| 5,480,422 A | 1/1996 | Ben-Haim |
| 5,546,951 A | 8/1996 | Ben-Haim |
| 5,558,091 A | 9/1996 | Acker et al. |
| 5,568,809 A | 10/1996 | Ben-Haim |
| 5,630,809 A | 5/1997 | Connor |
| 5,643,253 A | 7/1997 | Baxter et al. |
| 5,688,264 A | 11/1997 | Ren et al. |
| 5,693,043 A | 12/1997 | Kittrell et al. |
| 5,807,248 A | 9/1998 | Mills |
| 5,807,389 A | 9/1998 | Gardetto et al. |
| 5,830,209 A | 11/1998 | Savage et al. |
| 5,964,757 A | 10/1999 | Ponzi |
| 5,997,571 A | 12/1999 | Farr et al. |
| 6,016,452 A | 1/2000 | Kasevich |
| 6,053,912 A | 4/2000 | Panescu et al. |
| 6,071,302 A * | 6/2000 | Sinofsky ............... A61N 5/0601 606/15 |
| 6,106,516 A | 8/2000 | Massengill |
| 6,120,476 A | 9/2000 | Fung et al. |
| 6,143,018 A | 11/2000 | Beuthan et al. |
| 6,168,594 B1 | 1/2001 | LaFontaine et al. |
| 6,171,275 B1 | 1/2001 | Webster, Jr. |
| 6,171,303 B1 | 1/2001 | Ben-Haim et al. |
| 6,241,666 B1 | 6/2001 | Pomeranz et al. |
| 6,423,055 B1 | 7/2002 | Farr et al. |
| 6,464,694 B1 | 10/2002 | Massengill |
| 6,468,260 B1 | 10/2002 | Bumbalough et al. |
| 6,579,285 B2 | 6/2003 | Sinofsky |
| 6,602,242 B1 | 8/2003 | Fung et al. |
| 6,692,486 B2 | 2/2004 | Jaafar et al. |
| 6,736,808 B1 | 5/2004 | Motamedi et al. |
| 6,923,805 B1 | 8/2005 | LaFontaine et al. |
| 6,953,457 B2 | 10/2005 | Farr et al. |
| 8,500,730 B2 * | 8/2013 | Lee ...................... A61B 5/0084 606/41 |
| 8,861,020 B2 | 10/2014 | Imamura |
| 8,986,298 B2 * | 3/2015 | Lee ...................... A61B 5/0084 606/41 |
| 2001/0012429 A1 | 8/2001 | Wach et al. |
| 2002/0022834 A1 | 2/2002 | Simpson et al. |
| 2002/0026188 A1 | 2/2002 | Balbierz et al. |
| 2002/0045848 A1 | 4/2002 | Jaafar et al. |
| 2002/0183729 A1 | 12/2002 | Farr et al. |
| 2003/0004506 A1 | 1/2003 | Messing |
| 2003/0040657 A1 | 2/2003 | Yamaya et al. |
| 2003/0125730 A1 | 7/2003 | Berube et al. |
| 2004/0015061 A1 | 1/2004 | Currier et al. |
| 2004/0015138 A1 | 1/2004 | Currier et al. |
| 2004/0158302 A1 | 8/2004 | Chornenky et al. |
| 2005/0059962 A1 | 3/2005 | Phan et al. |
| 2005/0065504 A1 | 3/2005 | Melsky et al. |
| 2005/0070894 A1 | 3/2005 | McClurken |
| 2005/0096643 A1 | 5/2005 | Brucker et al. |
| 2005/0143721 A1 | 6/2005 | Brucker et al. |
| 2005/0143722 A1 | 6/2005 | Brucker et al. |
| 2005/0159734 A1 | 7/2005 | Brucker et al. |
| 2005/0165462 A1 | 7/2005 | Bays et al. |
| 2005/0171520 A1 | 8/2005 | Farr et al. |
| 2005/0222557 A1 | 10/2005 | Baxter et al. |
| 2005/0267372 A1 | 12/2005 | Hörnig |
| 2005/0267452 A1 | 12/2005 | Farr et al. |
| 2006/0030844 A1 | 2/2006 | Knight et al. |
| 2006/0122587 A1 | 6/2006 | Sharareh |
| 2006/0184165 A1 | 8/2006 | Webster, Jr. et al. |
| 2006/0229515 A1 | 10/2006 | Sharareh et al. |
| 2007/0287998 A1 * | 12/2007 | Sharareh ............ A61B 18/1492 606/41 |
| 2008/0097220 A1 | 4/2008 | Lieber et al. |
| 2008/0119694 A1 | 5/2008 | Lee |
| 2008/0154257 A1 | 6/2008 | Sharareh et al. |
| 2009/0005768 A1 | 1/2009 | Sharareh et al. |
| 2009/0005773 A1 | 1/2009 | Beeckler et al. |
| 2009/0131931 A1 | 5/2009 | Lee et al. |

FOREIGN PATENT DOCUMENTS

| | | |
|---|---|---|
| WO | WO 95/02995 | 2/1995 |
| WO | WO 2005/051215 A1 | 6/2005 |
| WO | WO 2007/127228 A2 | 11/2007 |
| WO | WO 2007/146995 A1 | 12/2007 |

OTHER PUBLICATIONS

Unpublished U.S. Appl. No. 11/281853, filed Nov. 17, 20015, in the name of Sharareh et al.
International Search Report and Written Opinion of the International Searching Authority, International Application No. PCT/US2007/071107, mailed Nov. 19, 2007.
European Search Report issued in EP Application No. 07254493.5 on Feb. 12, 2008, 4 pages.
Extended European Search Report dated Jun. 16, 2010 for EP Patent Application No. 10075155.1, 3 pages.
Partial European Search Report of EP Application No. 08253725.9, dated Apr. 22, 2009, 4 pages.

* cited by examiner

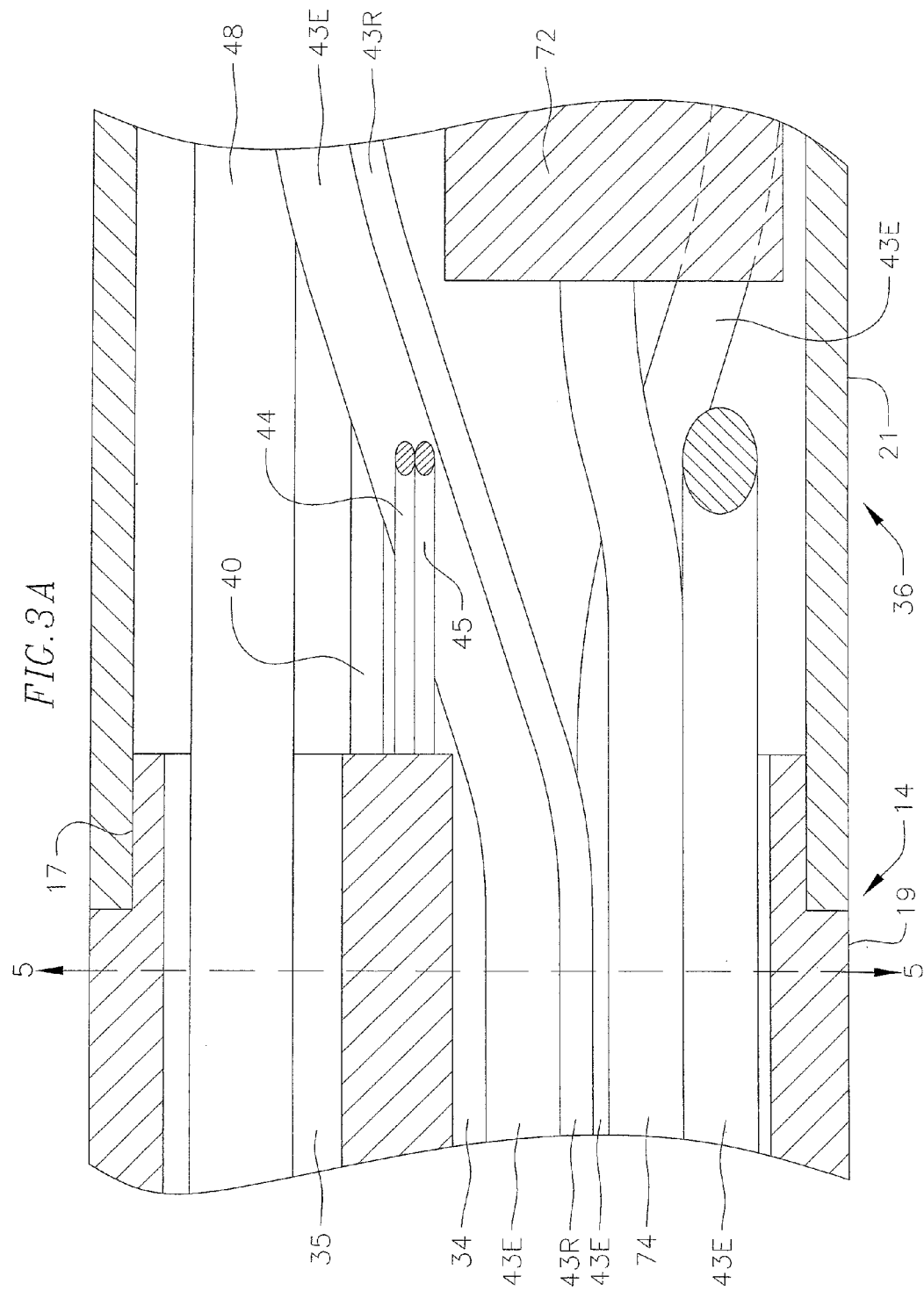

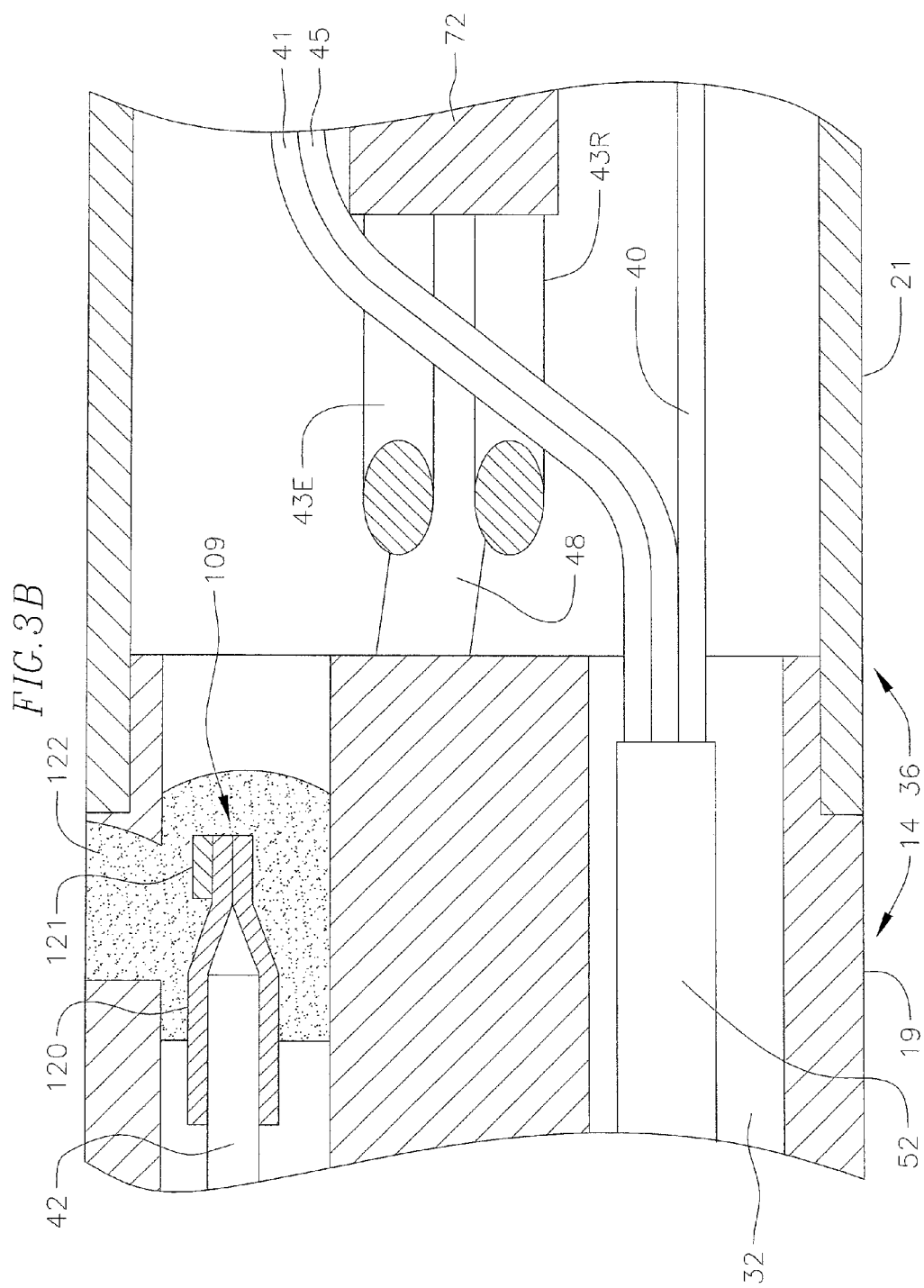

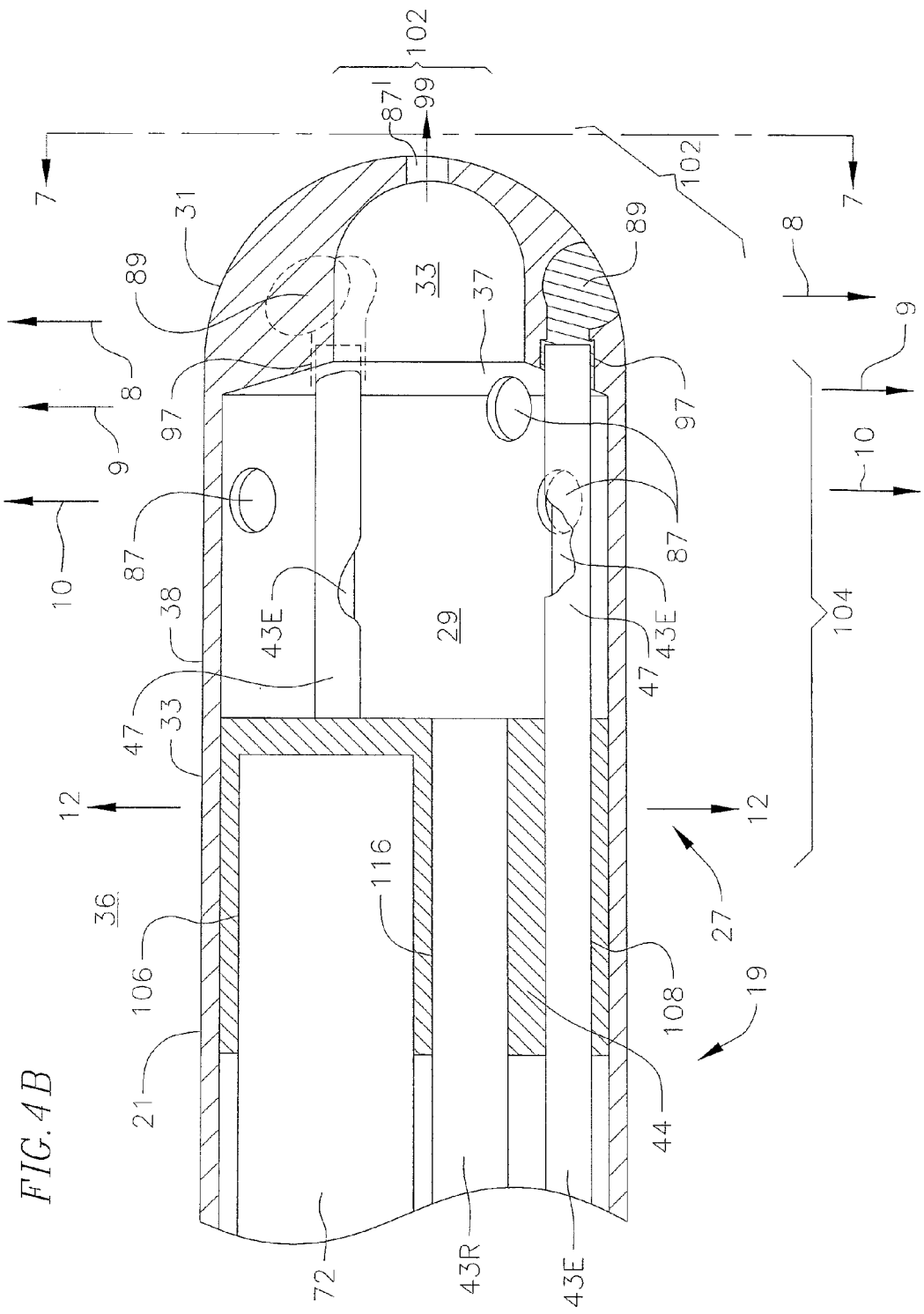

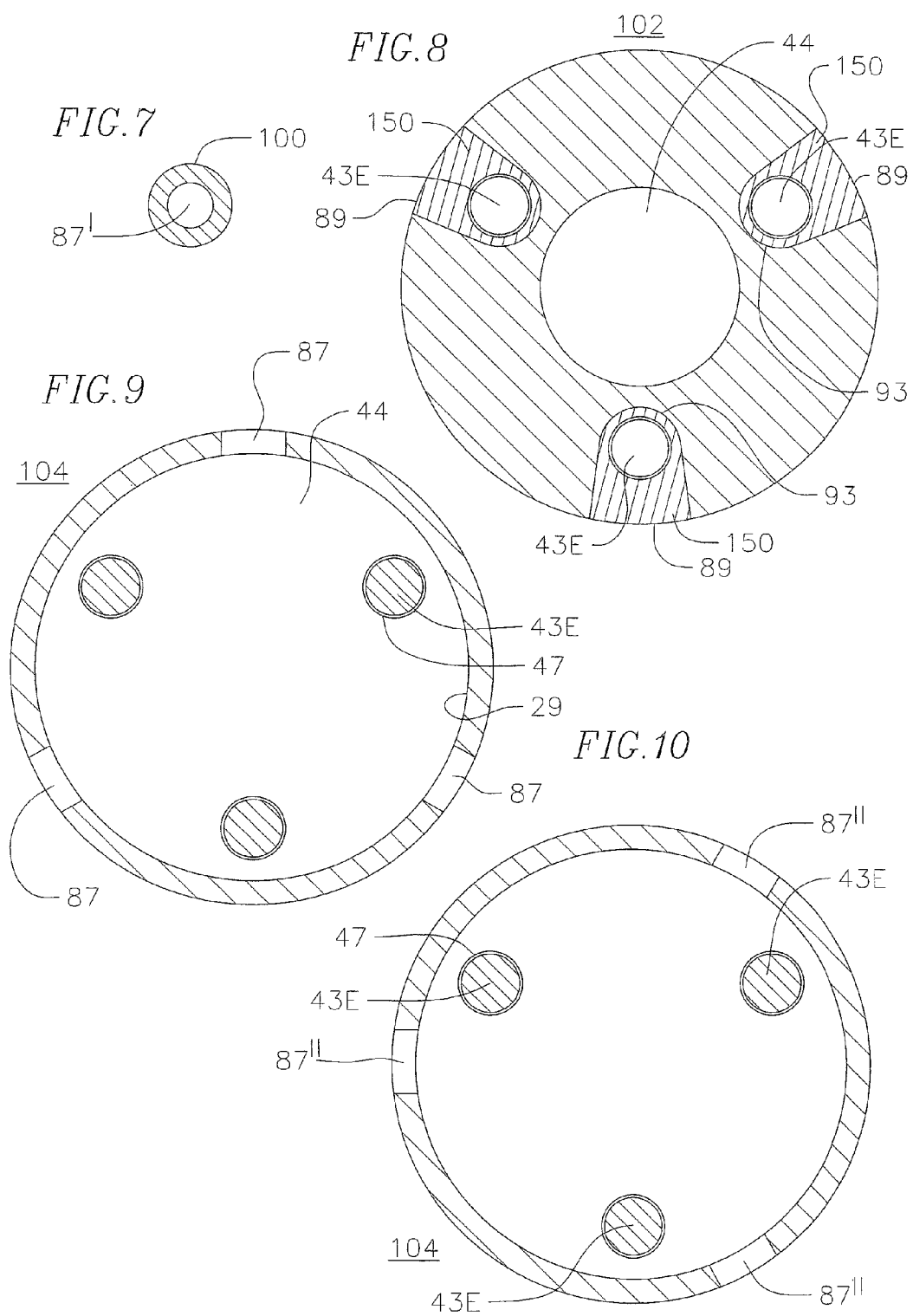

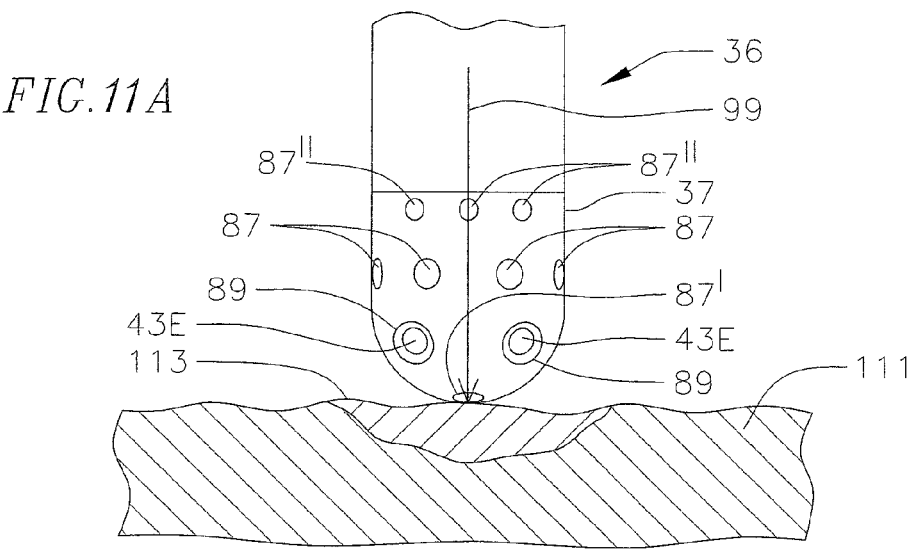
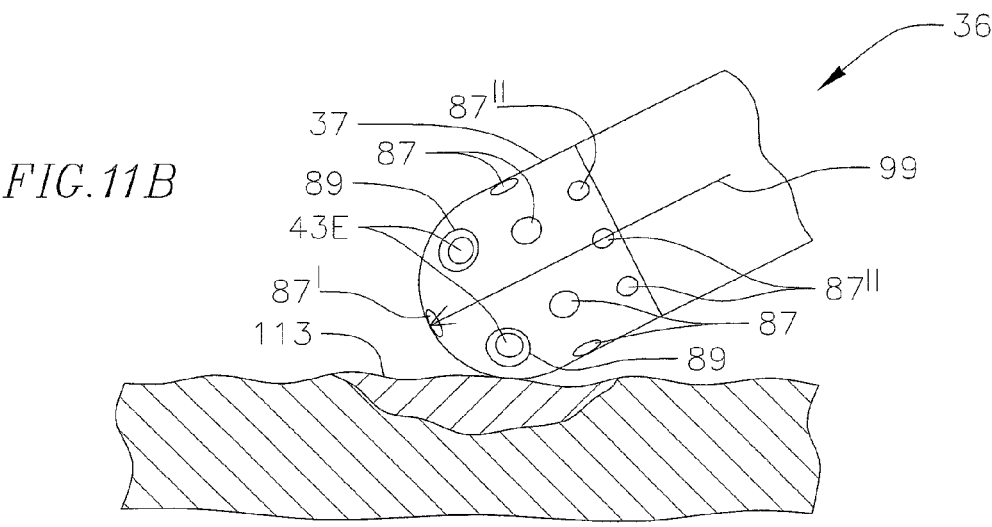
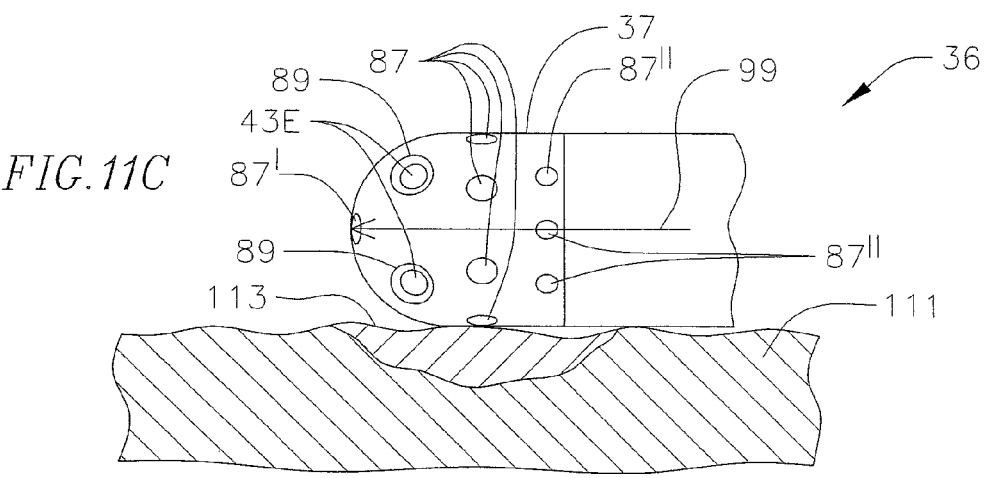

CATHETER WITH OMNI-DIRECTIONAL OPTICAL TIP HAVING ISOLATED OPTICAL PATHS

CROSS-REFERENCE TO RELATED APPLICATION

This application is a continuation of and claims priority to and the benefit of U.S. patent application Ser. No. 11/601,065 filed Nov. 17, 2006, now U.S. Pat. No. 8,986,298, the entire content of which is incorporated herein by reference.

FIELD OF INVENTION

The present invention relates to ablation catheters, and in particular to ablation catheters with optical monitoring of tissue.

BACKGROUND

For certain types of minimally invasive medical procedures, real time information regarding the condition of the treatment site within the body is unavailable. This lack of information inhibits the clinician when employing catheter to perform a procedure. An example of such procedures is tumor and disease treatment in the liver and prostate. Yet another example of such a procedure is surgical ablation used to treat atrial fibrillation. This condition in the heart causes abnormal electrical signals, known as cardiac arrhythmias, to be generated in the endocardial tissue resulting in irregular beating of the heart.

The most frequent cause of cardiac arrhythmias is an abnormal routing of electricity through the cardiac tissue. In general, most arrhythmias are treated by ablating suspected centers of this electrical misfiring, thereby causing these centers to become inactive. Successful treatment, then, depends on the location of the ablation within the heart as well as the lesion itself. For example, when treating atrial fibrillation, an ablation catheter is maneuvered into the right or left atrium where it is used to create ablation lesions in the heart. These lesions are intended to stop the irregular beating of the heart by creating non-conductive barriers between regions of the atria that halt passage through the heart of the abnormal electrical activity.

The lesion should be created such that electrical conductivity is halted in the localized region (transmurality), but care should be taken to prevent ablating adjacent tissues. Furthermore, the ablation process can also cause undesirable charring of the tissue and localized coagulation, and can evaporate water in the blood and tissue leading to steam pops.

Currently, lesions are evaluated following the ablation procedure, by positioning a mapping catheter in the heart where it is used to measure the electrical activity within the atria. This permits the physician to evaluate the newly formed lesions and determine whether they will function to halt conductivity. It if is determined that the lesions were not adequately formed, then additional lesions can be created to further form a line of block against passage of abnormal currents. Clearly, post ablation evaluation is undesirable since correction requires additional medical procedures. Thus, it would be more desirable to evaluate the lesion as it is being formed in the tissue.

A known method for evaluating lesions as they are formed is to measure electrical impedance. Biochemical differences between ablated and normal tissue can result in changes in electrical impedance between the tissue types. Although impedance is routinely monitored during electrophysiologic therapy, it is not directly related to lesion formation. Measuring impedance merely provides data as to the location of the tissue lesion but does not give qualitative data to evaluate the effectiveness of the lesion.

Another approach is to measure the electrical conductance between two points of tissue. This process, known as lesion pacing, can also determine the effectiveness of lesion therapy. This technique, however, measures the success or lack thereof from each lesion, and yields no real-time information about the lesion formation.

Thus, there is a need for a catheter that is capable of measuring lesion formation in real-time, if not monitoring tissue in general, and is adapted for use at most angles to the tissue. Moreover, where such measuring and detecting are accomplished through optical spectroscopy, there is a need for a catheter that can provide separate optical paths for illuminating the tissue and recapturing light from the tissue. The catheter should also be of a simplified but efficient design that allows for ease in manufacturing and reduced production labor and costs.

SUMMARY OF THE INVENTION

The present invention is directed to a catheter that enables real-time light measurements, for example, without limitation, diffuse reflectance, fluorescence, etc., from biological materials, such as tissue (including blood), while performing RF ablation. The catheter tip design is implied but maintains isolated illumination and collection paths within the tip electrode for light to exit the catheter tip and interact with, if not travel through, the tissue of interest (e.g., cardiac tissue or blood) before returning to the catheter tip. Such a design advantageously avoids saturation of the optical detector, and ensures diffusion of the illumination light within the medium of interest.

The light recaptured by the catheter from the tissue conveys tissue parameters that can be evaluated using optical spectroscopy. These parameters include, without limitation, lesion formation, depth of penetration of lesion, and cross-sectional area of lesion, formation of char during ablation, recognition of char during ablation, recognition of char from non-charred tissue, formation of coagulum around the ablation site, differentiation of coagulated from non-coagulated blood, differentiation of ablated from healthy tissue, tissue proximity, evaluation of tissue health, status, and disease state, and recognition of steam formation in the tissue for prevention of steam pop.

In accordance with the present invention, the catheter in one embodiment includes a catheter body and a tip electrode with a shell wall and a hollow cavity, where the shell wall has at least an illumination opening and a collection opening. The catheter also has a first fiber optic cable in communication with the illumination opening and a second fiber optic cable in communication with the hollow cavity, wherein light emitted from the first fiber optic cable exits the tip electrode to reach tissue through the illumination opening in defining a first path and returns to the tip electrode from the tissue into the hollow cavity through the collection opening in defining a second path. Advantageously, the first and second paths in the tip electrode are optically isolated from each other.

In a more detailed embodiment, a catheter has a catheter body and a tip electrode adapted for ablating tissue. The tip electrode has a shell and a hollow cavity. The shell has multiple illumination openings into which light from emitting fiber optic cables is injected to illuminate tissue of interest. The illumination openings have a semi-spherical cross-section and may be filled with a material with optical scattering properties, e.g., a scattering agent-filled epoxy or plastic, to aid in the even distribution of light out of the openings. The shell also has multiple collection openings through which light recaptured from the tissue is collected in the hollow cavity. And one or more receiving fiber optic cables are provided to receive the light collected in the hollow cavity. Where the emitting fiber optic cables traverse the hollow cavity, a coating is provided on the cables to prevent light from leaking out of or into the cables for keeping the separate paths optically isolated within the tip electrode.

As an omnidirectional illuminator and collector, the tip electrode in one embodiment has a first section that is generally perpendicular to a longitudinal axis of the tip electrode, a second section that is at an angle between about 0 and 90 degrees with the longitudinal axis, and a third section that is generally parallel with the longitudinal axis. The collection and illumination openings may be configured in any of the first, second and/or third sections. In one embodiment, the collection openings are configured in the first and third sections, and the illumination openings are configured in the second section.

The tip electrode also includes an alignment plug that seals the hollow cavity. The plug has passages for the emitting and the receiving fiber optic cables extending therethrough, to stabilize the fiber optic cables and minimize stress that can cause breakage of the fiber optic cables.

The present invention is also directed to a method of making an ablation tip electrode that also functions as an omnidirectional illuminator and collector. The method includes providing a shell with a hollow cavity, configuring at least one collection opening in the shell, configuring at least illumination opening in the shell, providing an emitting fiber optic cable adapted to emit light into the illumination opening, providing a receiving fiber optic cable adapted to receive light collected in the hollow cavity, and providing an optical barrier between the emitting fiber optic cable and the hollow cavity.

The method may further include providing the illumination opening with a semi-spherical cross section and filling the illumination opening with a material having optical scattering property, for example, a scattering agent-filled epoxy or plastic, to aid in the even distribution of light out of the openings. The method may also further include forming a plug to seal with hollow cavity, wherein the plug is configured with passages for the fiber optic cables to extend through, and fixedly securing portions of the fiber optic cables in the passages to the plug.

The present catheter and method are designed to use light in conjunction with irrigation and the technology of RF ablation. Advantageously, the light used to monitor and assess the tissue (or a lesion formed in the tissue) is generally not affected by the portion of the electromagnetic radiation used for ablation. Moreover, the bandwidth used for monitoring and assessing also transmits through blood with minimal attenuations. The fiber optics are used and disposed in the catheter in a manner that avoids contact with tissue, which can increase the operative lifetime of the catheter and minimize damages caused by abrasion to the fiber optics. Furthermore, the alignment plug in the tip electrode secures the fiber optic cables with minimal bend or strain but increased angular coverage, which can minimize fiber optics breakage during assembly and use, as well as reduce nonlinear optical effects caused by orientation of the fiber optics. In addition, the use of fiber optics to emit and receive light is a generally temperature neutral process that adds little if any measurable heat to surrounding blood or tissue.

BRIEF DESCRIPTION OF THE DRAWINGS

These and other features and advantages of the present invention will be better understood by reference to the following detailed description when considered in conjunction with the accompanying drawings wherein:

FIG. 3A is a side cross-sectional view of a catheter according to an embodiment of the invention, including the junction between the intermediate section and a tip section, taking along a first diameter.

FIG. 3B is a side cross-sectional view of a catheter according to an embodiment of the invention, including the junction between the intermediate section and a tip section, taking along a second diameter generally perpendicular to the first diameter of FIG. 3A.

FIG. 4B is a side cross-sectional view of a catheter according to an embodiment of the invention, including a junction between a plastic housing and a tip electrode, taken along the second diameter generally perpendicular to the first diameter of FIG. 4A;

FIG. 7 is a longitudinal cross-sectional view of the tip electrode of FIG. 4A, taken along line 7-7.

FIG. 8 is a longitudinal cross-sectional view of the tip electrode of FIG. 4A, taken along line 8-8.

FIG. 9 is a longitudinal cross-sectional view of the tip electrode of FIG. 4A, taken along line 9-9.

FIG. 10 is a longitudinal cross-sectional view of the tip electrode of FIG. 4A, taken along line 10-10.

FIG. 11A is a side view of another embodiment of a tip section whose longitudinal axis is generally perpendicular to tissue surface.

FIG. 11B is a side view of another embodiment of a tip section whose longitudinal axis is generally at an angle between zero and 90 to tissue surface.

FIG. 11C is a side view of another embodiment of a tip section whose longitudinal axis is generally parallel to tissue surface.

DETAILED DESCRIPTION OF THE INVENTION

Figure 1:
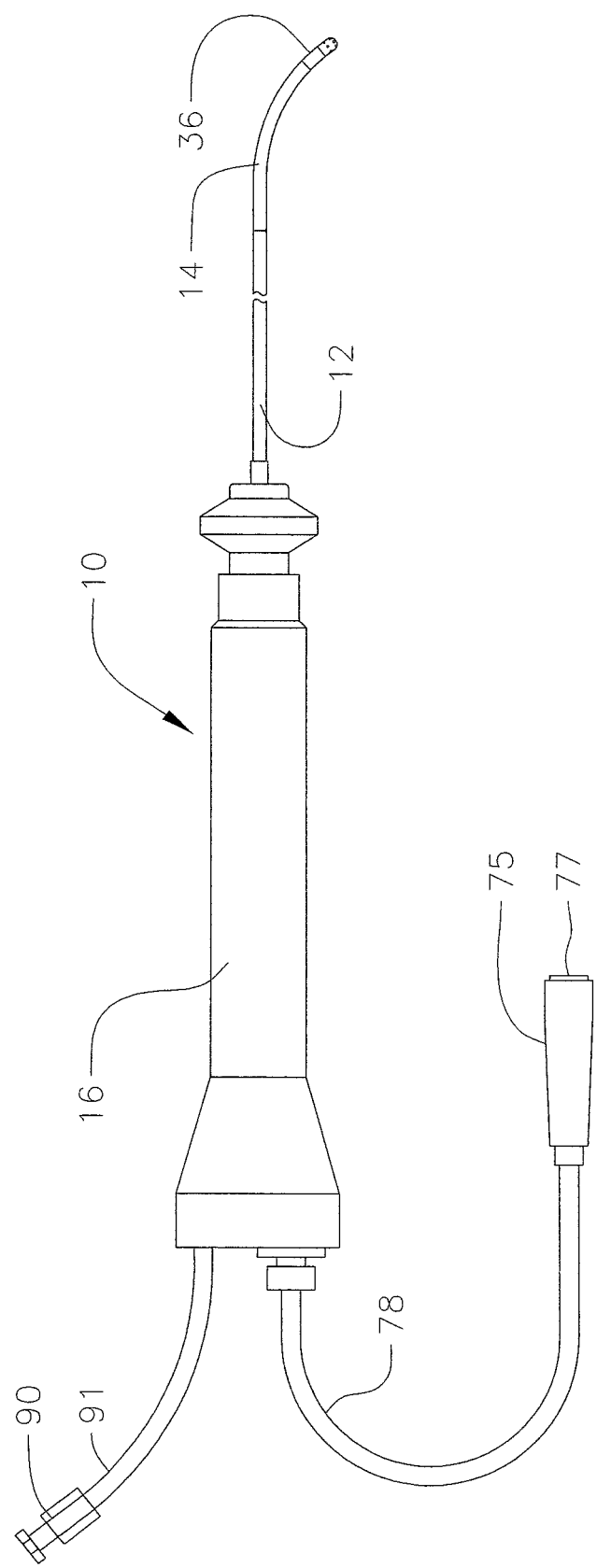
FIG. 1 is a side view of an embodiment of a catheter of the present invention.

The catheter 10 of the present invention is adapted to facilitate optically-based real-time assessment of ablation tissue characteristics, including without limitation, lesion formation, depth of penetration of the lesion, cross-sectional area of the lesion, formation of char during ablation, recognition of char during ablation, differentiation of char from non-charred tissue, formation of coagulum around the ablation site, differentiation of coagulated from non-coagulated blood, differentiation of ablated from healthy tissue, tissue proximity, and recognition of steam formation in the tissue for prevention of steam pop. These assessments are accomplished by measuring the light intensity at one or more wavelengths that is recaptured at the catheter resulting from the light radiated from the catheter tip onto ablated tissue. Fiber optic cables are provided in the catheter to transmit light to and from the catheter tip.

As shown in FIGS. 1-13, catheter 10 of the present invention comprises an elongated catheter body 12 having proximal and distal ends, a deflectable (uni- or bi-directionally) intermediate section 14 at the distal end of the catheter body 12, a tip section 36 at the distal end of the intermediate section, and a control handle 16 at the proximal end of the catheter body 12.

Figure 2A:
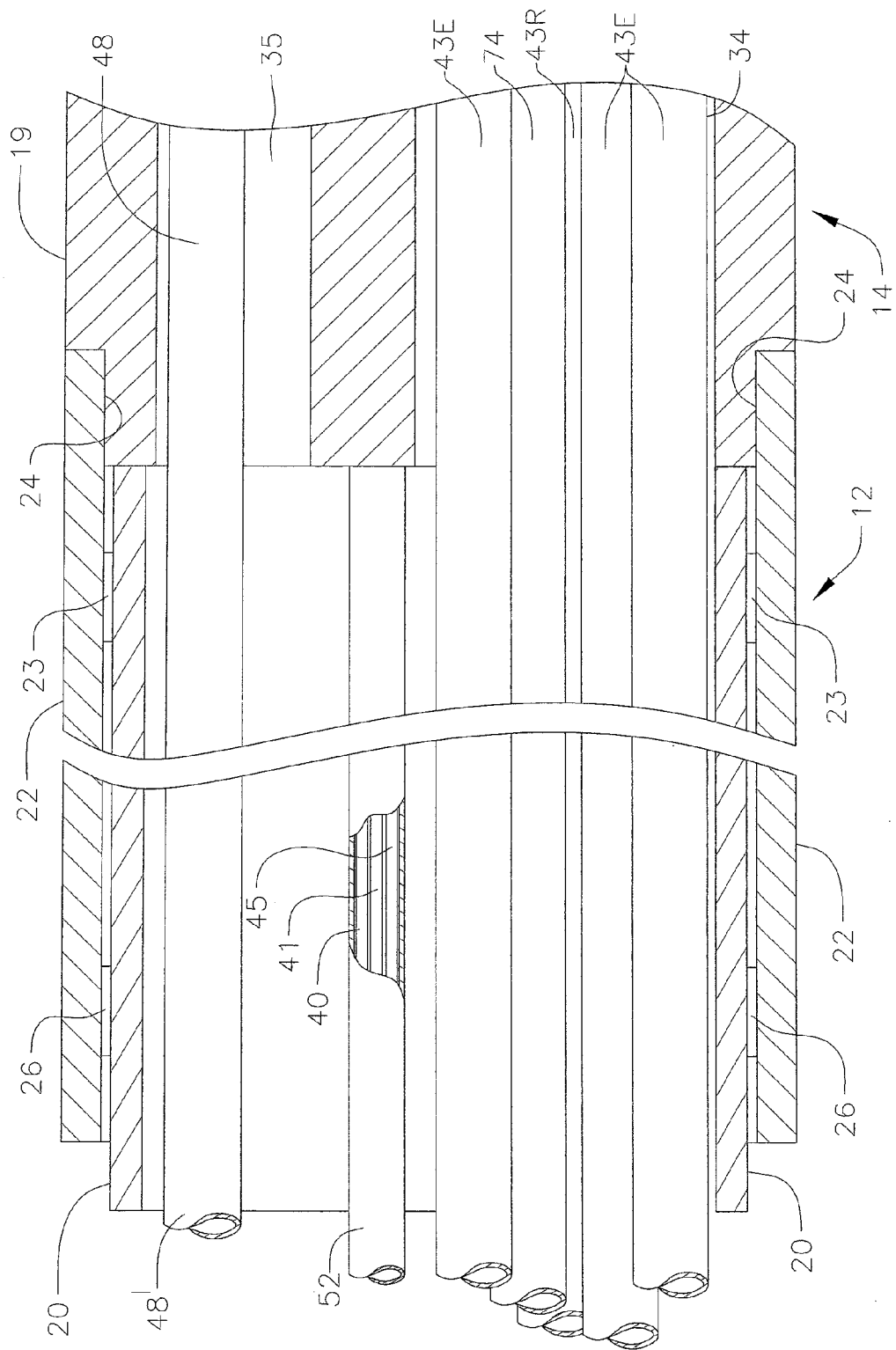
FIG. 2A is a side cross-sectional view of an embodiment of a catheter, including the junction between the catheter body and intermediate section, taken along a first diameter.
Figure 2B:
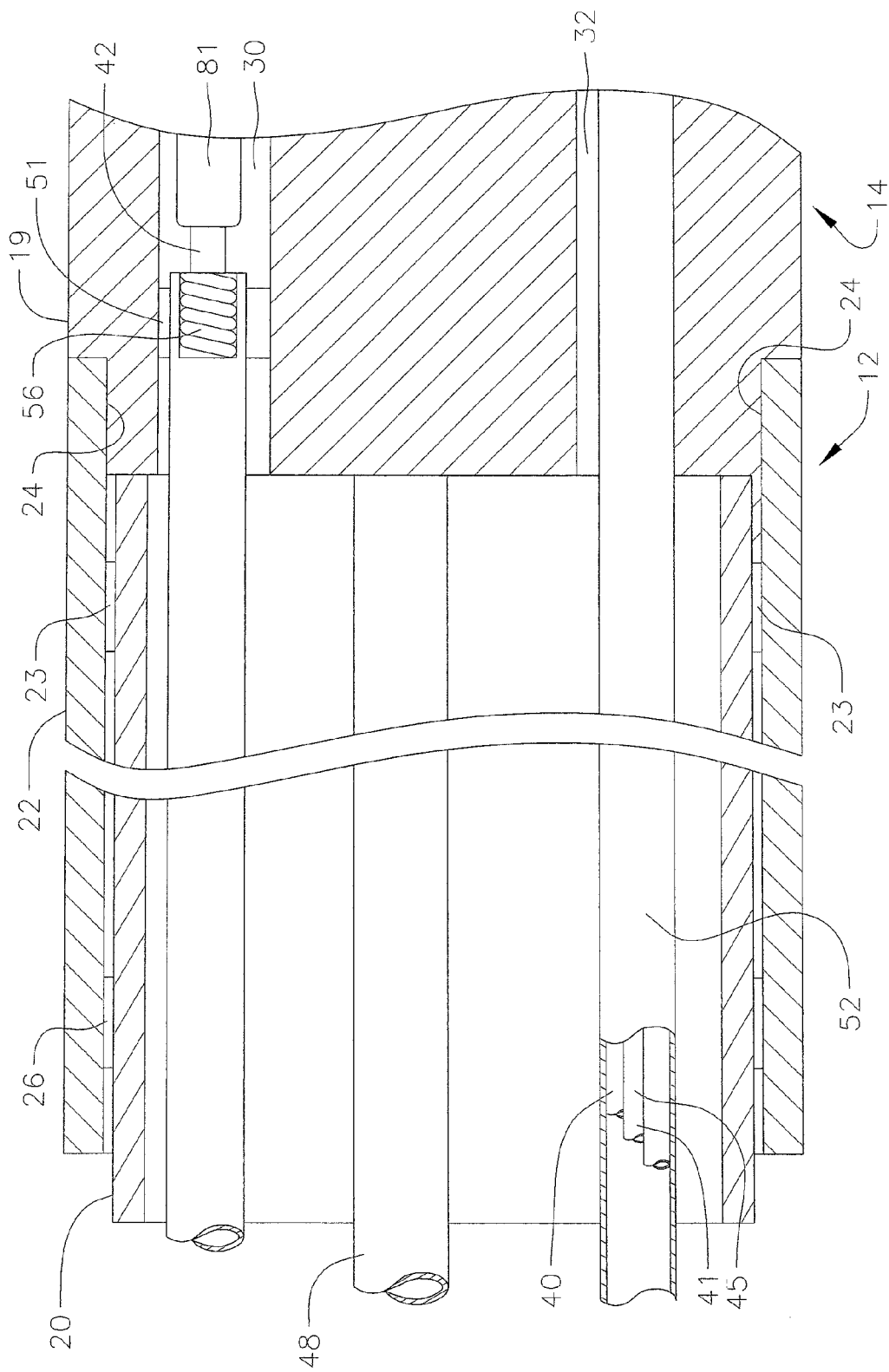
FIG. 2B is a side cross-sectional view of a catheter according to an embodiment of the invention, including the junction between the catheter body and intermediate section, taken along a second diameter generally perpendicular to the first diameter of FIG. 2A.

With additional reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A construction comprises an outer wall 22 made of an extruded plastic. The outer wall 22 may comprise an imbedded braided mesh of stainless steel or the like to increase torsional stiffness of the catheter body 12 so that, when the control handle 16 is rotated, the catheter body 12, the intermediate section 14 and the tip section 36 of the catheter 10 will rotate in a corresponding manner.

Extending through the single lumen 18 of the catheter body 12 are components, for example, wires, tubes and/or cables. A single lumen catheter body can be preferred over a multi-lumen body because it has been found that the single lumen body permits better tip control when rotating the catheter. The single lumen permits the various components to float freely within the catheter body. If such wires, tube and cables were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate the aforementioned components. The inner surface of the outer wall 22 may be lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing may be preferred for the stiffening tube 20 because it may be very thin walled while still providing very good stiffness. This maximizes the diameter of the central lumen 18 without sacrificing strength and stiffness.

The catheter may have an outer wall 22 with an outer diameter of from about 0.090 inch to about 0.098 inch and an inner diameter of from about 0.061 inch to about 0.078 inch and a polyimide stiffening tube 20 having an outer diameter of from about 0.060 inch to about 0.077 inch and an inner diameter of from about 0.051 inch to about 0.069 inch.

Figure 5:
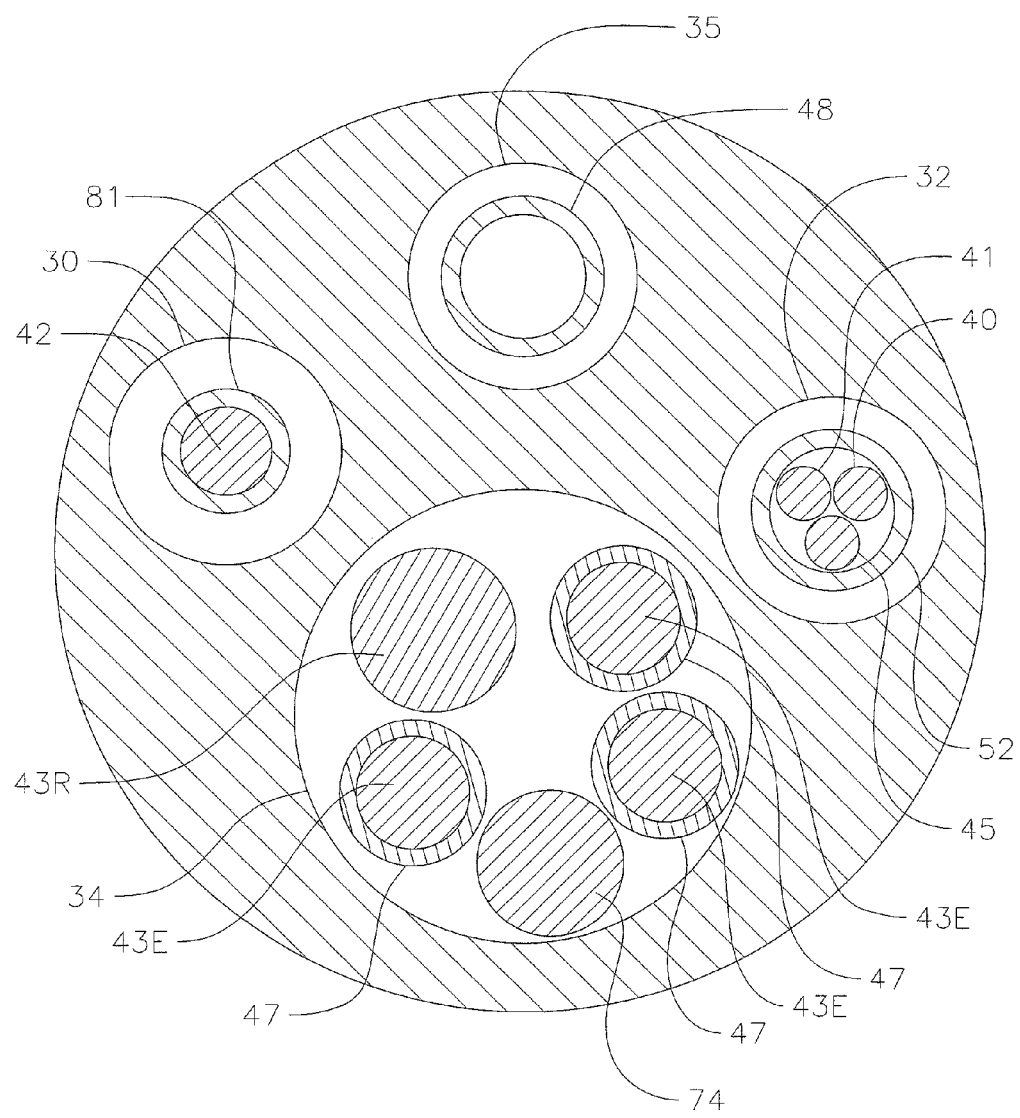
FIG. 5 is a longitudinal cross-sectional view of an embodiment of an intermediate section of FIG. 3A, taken along line 5-5.

Referring also to FIG. 5, the intermediate section 14 distal the catheter body 12 comprises a shorter section of tubing 19 having multiple lumens. The tubing 19 is made of a suitable non-toxic material that is preferably more flexible than the catheter body 12. A suitable material for the tubing 19 is braided or non-braided polyurethane. The outer diameter of the intermediate section 14, like that of the catheter body 12, is preferably no greater than about 8 french, more preferably 7 french. The size and number of the lumens are not critical. In an embodiment, the intermediate section 14 has an outer diameter of about 7 french (0.092 inch). The tubing 19 is multi-lumened, for example, with a first lumen 30, a second lumen 32, a third lumen 34 and a fourth lumen 35. In the illustrated embodiment, the lumens 30, 32 and 35 all have approximately the same diameter of about 0.22 inch, whereas the lumen 34 has a larger diameter of about 0.44 inch.

As shown in the embodiments of FIGS. 2A and 2B, the catheter body 12 that may be attached to the intermediate section 14 comprises an outer circumferential notch 24 configured in the proximal end of the tubing 19 that receives the inner surface of the outer wall 22 of the catheter body 12. The intermediate section 14 and catheter body 12 are attached by glue or the like. Before the intermediate section 14 and catheter body 12 are attached, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the intermediate section 14. If no compression coil is used, a force is applied to the proximal end of the stiffening tube 20, and, while the stiffening tube 20 is under compression, a first glue joint (not shown) is made between the stiffening tube 20 and the outer wall 22 by a fast drying glue, e.g. cyanoacrylate. Thereafter, a second glue joint 26 is formed between the proximal ends of the stiffening tube 20 and outer wall 22 using a slower drying but stronger glue, e.g., polyurethane.

If desired, a spacer can be located within the catheter body between the distal end of the stiffening tube and the proximal end of the tip section. The spacer provides a transition in flexibility at the junction of the catheter body and intermediate section, which allows this junction to bend smoothly without folding or kinking. A catheter having such a spacer is described in U.S. patent application Ser. No. 08/924,616, entitled "Steerable Direct Myocardial Revascularization Catheter", the entire disclosure of which is incorporated herein by reference.

Figure 4A:
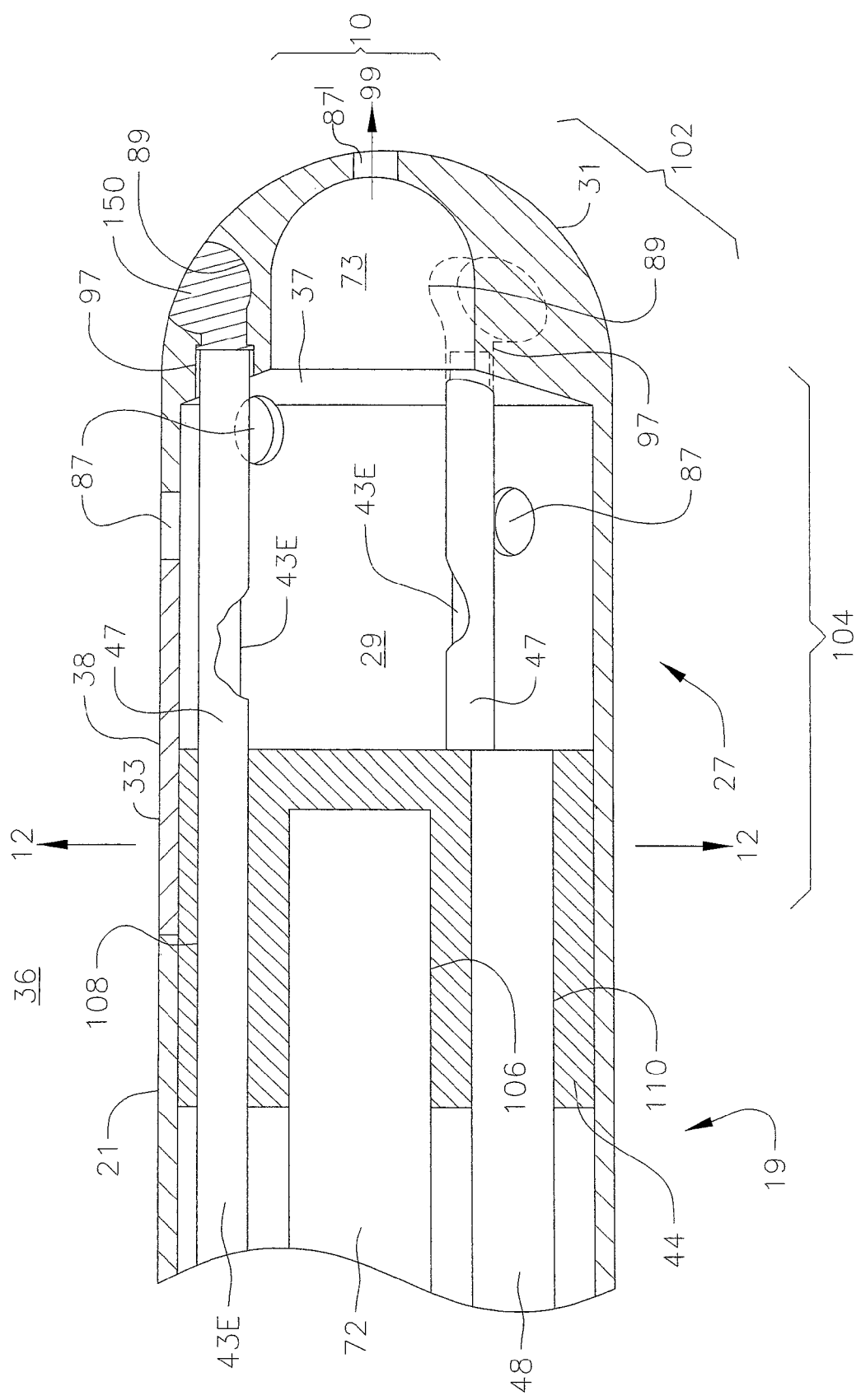
FIG. 4A is a side cross sectional view of a catheter according to an embodiment of the invention, including a junction between a plastic housing and a tip electrode, taken along a first diameter.

Extending from the distal end of the intermediate section 14 is the tip section 36 that includes a tip electrode 27 and a plastic housing 21, as shown in FIGS. 4A and 4B. The plastic housing 21, as also shown in FIGS. 3A and 3B, connects the tip electrode 27 and the tubing 19, and provides housing and/or transitional space for the components that extend into or through its lumen, as discussed further below. The plastic housing 21 is preferably made of polyetheretherketone (PEEK) and may be about 1 cm long. Its proximal end receives the outer circumferentially notched surface 17 of the tubing 19 of the intermediate section 14. The intermediate section 14 and the plastic housing 21 are attached by glue or the like. Components such as wires, cables and tubes that extend between the intermediate section 14 and the tip electrode 27 help keep the tip electrode in place.

In accordance with the present invention, the tip electrode 27 is adapted to function as an omnidirectional illuminator and collector for recapturing light that is radiated from the catheter tip onto ablated tissue. As shown in FIGS. 4A and 4B, the tip electrode comprises a shell wall 38 and a plug 44. The shell 38 is configured with a distal dome end 31 and an open proximal portion 33 in communication with a hollow cavity 29. In the illustrated embodiment, the shell wall 28 has a generally uniform thickness except at the distal dome end 31 where the thickness is greater and surrounds a distal dome cavity 73 extending from a rim region 37 of the hollow cavity 29. The distal dome end 31 of the shell is atraumatic and adapted for contact with tissue. The open proximal end 33 is configured to receive the plug 44 which, among other functions, seals the hollow cavity 29.

The shell 38 and the plug 44 are formed from any suitable material that is opaque and/or reflective, and both thermally and electrically conductive which allows for radio frequency ablation using an RF generator. Such suitable materials include, without limitation, platinum-irridium, platinum, gold alloy, or palladium alloy.

Figure 6:
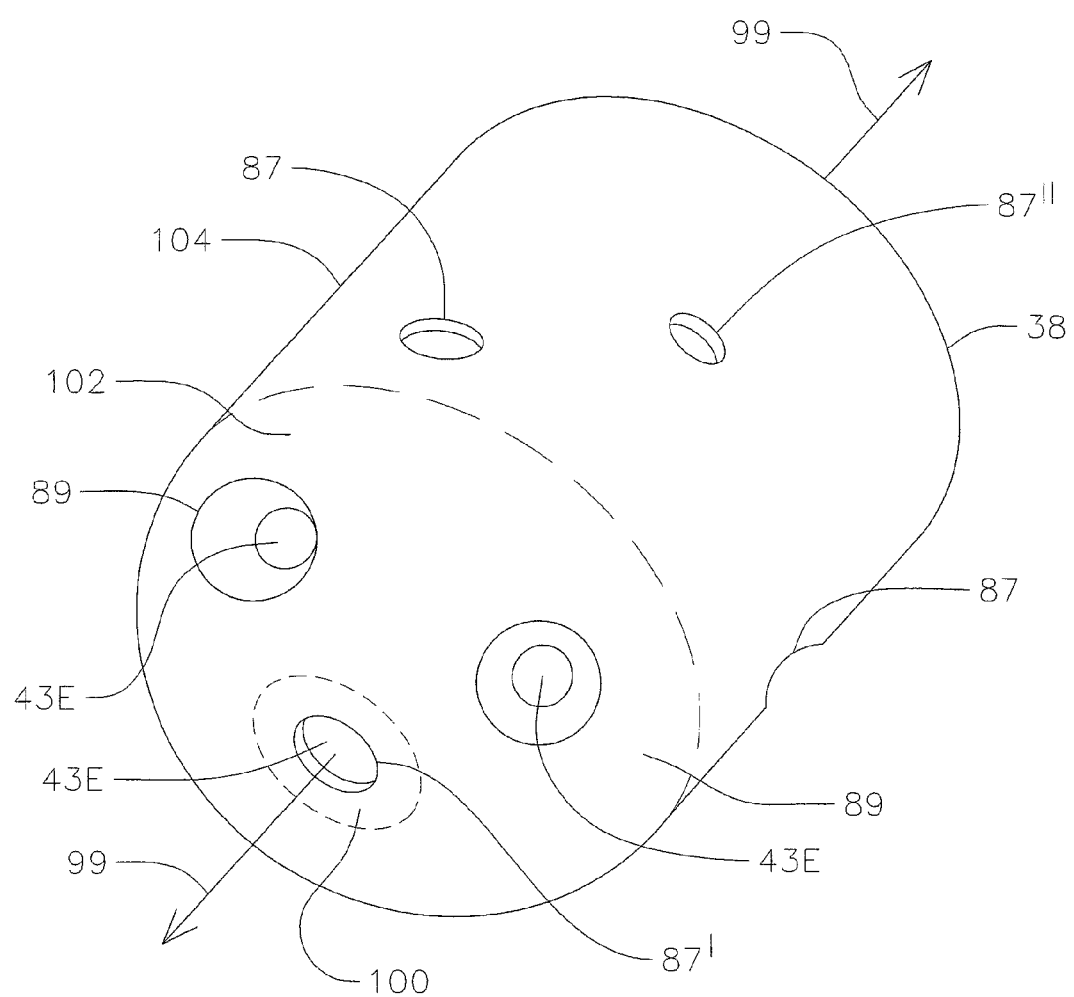
FIG. 6 is a perspective view of an embodiment of a tip electrode.

The tip electrode 27 has different sections relative to its longitudinal axis 99 in rendering the tip omnidirectional for optical tissue monitoring. As shown in FIGS. 4A, 4B, and 6, there are a distal section 100, a mid-section 102 and a proximal section 104. The shell wall 38 of the distal section 100 is generally perpendicular to the axis 99. The shell wall of the mid-section 102 is generally at an angle ranging between zero and 90 degrees, preferably about 30 to 60 and more preferably about 45 degrees to the axis 99. The shell wall of the proximal section 104 is generally parallel with the axis 99. These differently-angled sections which have a generally smooth and atraumatic transition between each other enable the tip electrode 27 to operate as an illuminator and a collector for various angles between the tip section 36 and the tissue as shown in FIGS. 11A-11C.

The shell wall 38 has a plurality of holes or openings of various sizes, including illumination openings and collection openings for light to leave and re-enter the tip electrode 27. As discussed further below, the tip electrode 27 provides optically-isolated paths for light intended to illuminate tissue and for light that is received through the collection openings. Each section 100, 102, 104 of the tip electrode can have any number of illumination and/or collection openings as desired or appropriate, although the number is dependent in part on the size of the tip electrode and the size and number of fiber optic cables housed therein. In the illustrated embodiment, the distal section 100 has a collection opening 87' at the distal end of the tip electrode along the longitudinal axis 99 (FIG. 7). The mid-section 102 has three illumination openings 89 that are equi-angular from each other at about 120 degrees radially about the axis (FIG. 8). The proximal section 104 has three more collection openings 87 that are equi-angular from each other at about 120 degrees radially about the axis (FIG. 9). The three collection openings 87 are offset radially by about 20 degrees from the three illumination openings 89 in the mid-section 102 Also in the proximal section 104 further proximal to the three collection openings 87 are an additional three collection openings 87" (FIG. 10) that are equi-angular from each other at about 120 degrees about the axis. These three collection openings 87" are offset radially by about 40 degrees from the more distal collection openings 87 in the proximal section 104.

To efficiently illuminate the tissue of interest, each of the illumination openings 89 has a generally curved cross-section. In the illustrated embodiment of FIG. 8, the cross-section has a semi-spherical apex 93 where the overall cross-section can be described as parabolic. The semi-spherical apex efficiently reflects light out of the opening 89 for a more even distribution of light from the distal dome end 31 of the tip electrode 27.

With reference to FIGS. 4A and 4B, light is delivered to the illumination openings 89 by one or more emitting fiber optic cables 43E whose distal ends are received in passages 97 extending longitudinally from the rim section 37 of the hollow cavity 49. The configuration of the passages further isolates the light from the cables 43E from the cavity 29, and vice versa. The illumination openings 89 may be filled with a material 150 with optical scattering properties, e.g., a scattering agent-filled epoxy or plastic to aid in the even distribution of light out of the openings 89. Accordingly, light is emitted omnidirectionally onto the tissue of interest from the distal end of the tip electrode with minimal loss to absorption within the tip dome structure and the material 150 used to scatter the light.

Light reentering the tip electrode from the tissue via the collection openings 87 is captured and reflected about in the hollow cavity 29. The distal dome cavity 33 connecting the opening 87' and the hollow cavity 29 is configured to optimize the amount of light received in the hollow cavity 29 through the collection opening 8T. At least one receiving fiber optic cable 43R extends into the hollow cavity to collect the light. It is noted that because each of the emitting fiber optic cables 43E traverses the hollow cavity 29 to reach the passage 97, each cable 43E has a coating 47 to optically isolate itself from the cavity, and vice versa. The coating can be an opaque but reflective buffer material, e.g., aluminum, gold and the like, so that light cannot penetrate the side wall of the fiber 43E either into the cavity 29 or from the cavity. The coating may extend the length of the fibers 43E throughout the catheter.

The fiber optic cables 43E and 43R are protectively housed in the catheter from the control handle 16 to the tip section 36. As shown in FIGS. 2B and 5, they extend through the central lumen 18 of the catheter 12, the third lumen 34 of the intermediate section 14, the plastic housing 21 and into the tip electrode 27.

In the disclosed embodiment, there are three illuminating cables 43E and one receiving cable 43R. The cables 43E function as light emitters by transmitting light to the tip electrode 37 from a remote light source. The cable 43R functions as a light receiver by collecting light from the hollow cavity 29 in the tip electrode 27. It is understood by one of ordinary skill in the art that optical waveguides and fiber optic cables in general serve to transmit optical energy from one end to the other, although these are not exclusive.

Formed of the same or comparable material as the shell 38, the plug 44 has a generally elongated cylindrical configuration having a predetermined length, and a generally circular cross-section that matches the cross-section of the open proximal end 33 of the tip electrode 27. A distal portion of the plug 44 is press fitted, or fixed with solder into the open proximal end 33 to seal the hollow cavity 29, while a proximal portion of the plug 44 extends proximally from the tip electrode 27 for attachment to the housing 21.

In accordance with the present invention, blind holes and passages are provided in the plug 44 to allow components extending from the intermediate section 14 to be anchored to the plug or to pass through to the hollow cavity 29. In the illustrated embodiment of FIGS. 4A, 4B and 12, there are blind holes 102, 104 and 106 formed in the proximal surface of the plug in which distal ends of a lead wire 40, thermocouple wires 41 and 45 and a location sensor 72 are anchored, respectively. There are also passages 108, 112, 114, and 116 through which the fiber optic cables 43E and 43R extend, and a passage 110 through which an irrigation tube 48 extends into the hollow cavity of the tip electrode 29. The passages 108, 112 and 114 for three fiber optic cables 43E are generally aligned with the passages 97 leading to the illumination openings 89 in the shell wall 38 of the tip electrode. The portions of the components extending through the passages in the plug 44 are securely fixed in the passages to the plug 44 by glue, adhesive or the like. As such, the passages and the plug help align, stabilize and secure the various components extending through the plug 44. In particular, the passages help minimize stress on the cables 43E and 43R in their transition between the intermediate section 14 and the tip electrode 27.

In accordance with the present invention, illumination of tissue 111 and recapturing of the light from the tissue is accomplished by the omnidirectional tip electrode 27 whether the catheter 10 is generally perpendicular to the tissue (FIG. 11A), at an angle between about zero and ninety degrees (FIG. 11B), or generally parallel with the tissue (FIG. 11C). It is understood by one of ordinary skill in the art that the plurality and configuration of the sections 100, 102 and 104 and of the collection and illumination openings 87, 87' and 87" and 89 may be varied as appropriate or desired. The size and dimensions of each section may also be varied as appropriate or desired, as well as the shape of the openings, which can be round, ovular, square, polygonal, flat (slit), or any combination of these shapes.

In operation, the catheter 10 emits light at its tip electrode 27 as provided by the fiber optic cables 43E at their distal ends which emit light into the illumination openings 89, where the semi-spherical apex 93 efficiently reflects light out of the opening 89 for a more even distribution of light from the distal dome end 31 of the tip electrode 27. As lesion 113 forms in the tissue 111 from ablation carried out by tip electrode 27 of the catheter 10 (or by another catheter), its characteristics are altered as understood by one of ordinary skill in the art. In particular, as the lesion is illuminated by light, the light is scattered and/or reflected back toward the tip electrode 27, where such light having interacted or otherwise having been affected by the lesion bears qualitative and quantitative information about the lesion 113 as it is recaptured by the hollow cavity 29 via the collection openings 87, 87', 87" of the tip electrode. Light recaptured from the tissue is collected in the hollow cavity 29 of the tip electrode. The receiving fiber optic cable 43R receives the recaptured light which bears the qualitative and quantitative information and is transmitted to an optical processing system, as described below in further detail.

In accordance with the present invention, the tip electrode 27 provides separate optical paths for the light that illuminates tissue and the light recaptured from the tissue which are optically isolated from each other by the shell wall 38, the passages 97 and/or the coating 47 on the emitting fiber optic cables 43E. The optical path from the tip electrode to the tissue begins with light that is injected into the illumination openings 89 via the fiber optic cables 43E which is reflected by the semi-spherical apex 93 and diffusely scattered by the filler 150 into multiple angles and directions before exiting the illumination openings 89 of the tip electrode 37. Exiting the tip electrode 27 from the illumination openings 89, the light is incidental on the tissue of interest, interacts with the tissue and is reflected or scattered back to the tip electrode from the tissue. The separate optical path from the tissue back to the tip electrode begins with entry through the collection openings 87 and then collection in the hollow cavity 29 where the light is received by the fiber optic cable 43E.

It is understood that the fiber optic cables 43E and 43R may be any suitable optical wave guide wherein light introduced at one of the cable is guided to the other end of the cable with minimal loss. Each of the cables 43E and 43R may be a single fiber optic cable or fiber bundles. They may be single mode (also known as mono-mode or uni-mode), multi-mode (with step index or graded index) or plastic optical fiber (POF), depending on a variety of factors, including but not limited to transmission rate, bandwidth of transmission, spectral width of transmission, distance of transmission, diameter of cable, cost, optical signal distortion tolerance and signal attenuation, etc. Moreover, light delivery and collection may be accomplished with other devices, such as air-core fibers, hollow waveguides, liquid waveguides and the like.

Included in the present invention is a method for manufacturing the tip electrode 27. The method includes providing a rod of a suitable diameter and length, constructed of a suitable material that is thermally and electrically conductive which allows for radio frequency ablation using an RF generator. Such suitable material may include, without limitation, platinum-irridium, platinum, gold alloy, or palladium alloy. To form the shell 38, the distal end of the rod is turned to form the distal dome end 31 and the interior is drilled in the longitudinal direction of the rod from the proximal end 33 to form the hollow cavity 29 and the distal dome cavity 73. The term drilling as used herein includes mechanical drilling, chemical or laser etching, or the like.

The passages 97 are also drilled in the rim region 37 from the proximal end 33 through the hollow cavity 29 toward the distal dome end 31. The illumination openings 89 are drilled radially from outside the shell 38 through to the passages 97. It is understood that the illumination openings 89 can be drilled before or after the drilling of the passages 97, so long as the two structures connect and are in communication, and in turn, the hollow cavity 29 and the outside of the tip electrode are in communication with each other via the passages 97 and the illumination openings 89.

The collection openings 87, 87', 87" are also drilled radially from outside the shell 38 so there is communication between outside the tip electrode and the hollow cavity 29. The openings 87 can be formed before or after the formation of the illumination openings 89 and passages 97.

To form the plug, a rod of the aforementioned suitable material with a suitable diameter and length is provided. The passages 108, 112, 114 and 116 for the fiber optic cables 43 are drilled. The plug is press-fitted or soldered into the proximal opening of the tip electrode, but preferably after the fiber optic cables 43E and 43R are received in the passages 108, 112, 114 and 116 and the fiber optic cables 43E are inserted into the passages 97. After the plug 44 is press-fitted or soldered into the shell 38, glue, adhesive or the like is injected into the passages 108, 112 and 116 to fix the portions of the fiber optic cables extending through the passages. These fixed portions secure the fiber optic cables, particularly those of cables 43E, stationary within the tip electrode as a measure against breakage in or detachment from the tip electrode. The blind holes and other passages in the plug can be drilled before or after the plug is press-fitted into the shell 38. Methods for manufacturing a shell and a plug are disclosed in Ser. No. 11/058,434; filed Feb. 14, 2005, the entire disclosure of which is hereby incorporated by reference.

The shell 28 of the tip electrode 27 may have an actual length, i.e., from its distal end to its proximal end, between about 2.0 mm to about 8.0. The plug 44 of the tip electrode may have an actual length, i.e., from its distal end to its proximal end, between about 1.0 mm to about 4.0 mm. The tip electrode as a combination of the shell and the plug may have an actual length, i.e., from its distal end to its proximal end, between about 2.5 mm to about 11 mm. Preferably the tip electrode 27 has a diameter about the same as the outer diameter of the tubing 19 of the intermediate section 14.

Figure 12:
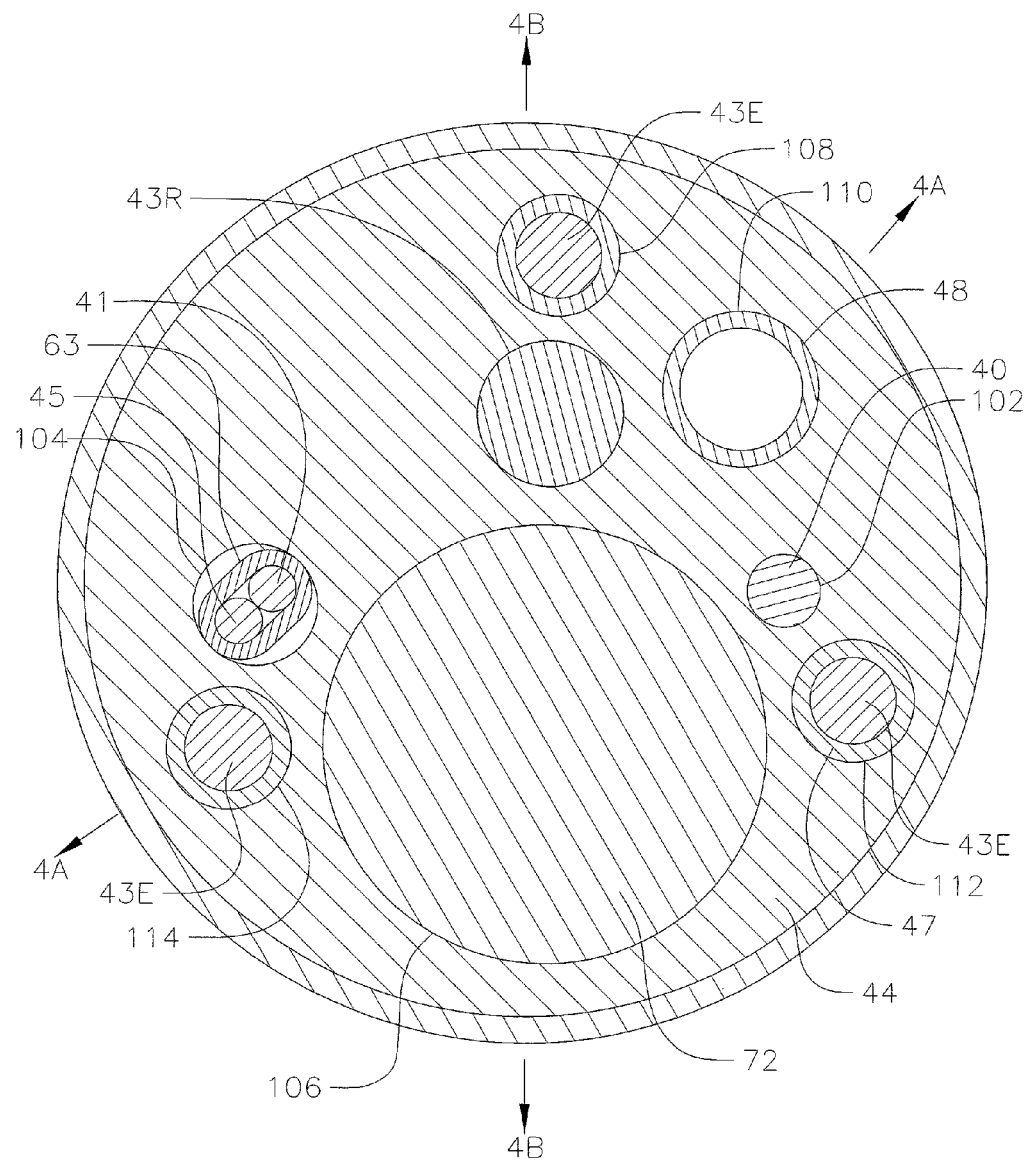
FIG. 12 is a longitudinal cross-sectional view of the plug within the tip electrode of FIG. 4A, taken along line 12-12.

To keep the collection openings of the tip electrode 27 generally free from obstruction from blood or other bodily fluids and tissue encountered by the tip electrode 37, the tip electrode is irrigated with fluid, e.g., saline, that is fed into the hollow cavity by an irrigation tube 48, as shown in FIG. 4A. The irrigation tube 48 extends through the cental lumen 18 of the catheter body 12 (FIG. 2A), the fourth lumen 35 of the intermediate section 14 (FIG. 3), through the plastic housing 21 and passage 110 in the plug 44 (FIG. 12). The tube 48 is anchored in the passage 110 and in the fourth lumen 35 by polyurethane glue or the like. The proximal portion of the tube 48 extends through the control handle 16 and terminates in a luer hub 90 (FIG. 1) or the like at a location proximal to the control handle. In the disclosed embodiment, the irrigation tube 48 transitions from a smaller diameter at the distal end to a larger diameter at the proximal end. For example, a distal segment can be about 0.0155×0.0175 inches and a proximal segment can be about 0.024×0.28 inches. In practice, fluid may be injected by a pump (not shown) into the irrigation tube 48 through the luer hub 90, and into the hollow cavity 29 in the tip electrode 27, and out the collection openings. The infusion tube 48 may be made of any suitable material, and is preferably made of polyimide tubing.

In accordance with a feature of the present invention, the pump maintains the fluid at a positive pressure differential relative to outside the hollow cavity 29 so as to provide a constant unimpeded flow or seepage of fluid outwardly from the hollow cavity 29 which continuously flushes the collection openings and minimizes obstruction so light can freely pass through for the aforementioned light collection purposes. In addition to the above, the irrigation adaptation of the catheter 10 may serve other typical functions such as cooling the tip electrode and/or the ablation site and increasing conduction for deeper and larger lesions.

Figure 12A:
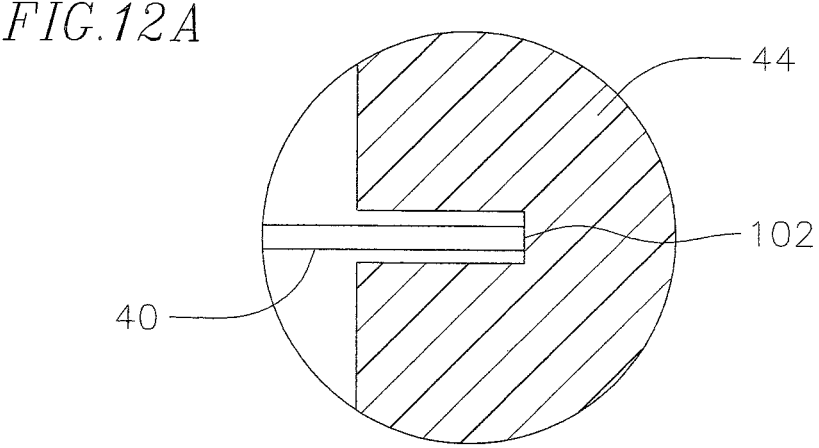
FIG. 12A is a detailed cross-sectional view of an embodiment of a distal end of a lead wire anchored in a plug of a tip electrode.
Figure 12B:
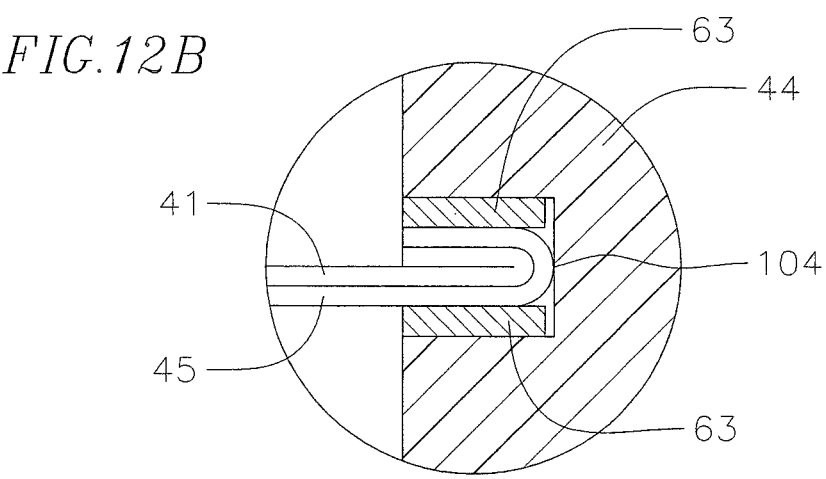
FIG. 12B is a detailed cross-sectional view of an embodiment of distal ends of a thermocouple wire pair anchored in a plug of a tip electrode.

To energize the tip electrode 27 for RF ablation, the lead wire 40 is anchored in the plug 44. With reference to FIGS. 1, 2A and 5, the lead wire 40 extends through the second lumen 32 of intermediate section 14, the central lumen 18 of the catheter body 12, and the control handle 16, and terminates at its proximal end in an input jack (not shown) that may be plugged into an appropriate monitor (not shown). The portion of the lead wire 40 extending through the central lumen 18 of the catheter body 12, control handle 16 and distal end of the intermediate section 14 is enclosed within a protective sheath 52, which can be made of any suitable material, preferably Teflon®. The protective sheath 52 is anchored at its distal end to the distal end of the intermediate section 14 by gluing it in the lumen 32 with polyurethane glue or the like. The lead wire 40 is attached to the tip electrode 27 by any conventional technique. In the illustrated embodiment, connection of the lead wire 40 to the tip electrode 27 is accomplished, for example, by welding the distal end of the lead wire 40 into the blind hole 102 (FIGS. 12 and 12A) in the plug 44 of the tip electrode 27.

A temperature sensing means is provided for the tip electrode 27 in the disclosed embodiment. Any conventional temperature sensing means, e.g., a thermocouple or thermistor, may be used. With reference to FIGS. 12. and 12B, a suitable temperature sensing means for the tip electrode 27 comprises a thermocouple formed by a wire pair. One wire of the wire pair is the copper wire 41, e.g., a number 40 copper wire. The other wire of the wire pair is the constantan wire 45, which gives support and strength to the wire pair. The wires 41 and 45 of the wire pair are electrically isolated from each other except at their distal ends where they contact and are twisted together, covered with a short piece of plastic tubing 63, e.g., polyimide, and covered with epoxy. The plastic tubing 63 is then attached in the hole 104 of the plug 44, by epoxy or the like. As shown in FIGS. 2A, 3 and 5, the wires 41 and 45 extend through the second lumen 32 in the intermediate section 14. Within the catheter body 12 the wires 41 and 45 extend through the central lumen 18 within the protective sheath 52 along with the lead wires 40. The wires 41 and 45 then extend out through the control handle 16 and to a connector (not shown) connectable to a temperature monitor (not shown). Alternatively, the temperature sensing means may be a thermistor. A suitable thermistor for use in the present invention is Model No. AB6N2-GC14KA143T/37C sold by Thermometrics (New Jersey).

The embodiment of the catheter disclosed herein is unideflectional, having a single puller wire; however, it is understood by one of ordinary skill in the art that the catheter may be bi-directional with two puller wires. Referring to FIG. 2B, the puller wire 42 for deflecting the intermediate section 14 extends through the catheter body 12 and is anchored at its proximal end to the control handle 16. The puller wire is made of any suitable metal, such as stainless steel or Nitinol, and is preferably coated with Teflon® or the like. The coating imparts lubricity to the puller wire. The puller wire preferably has a diameter ranging from about 0.006 to about 0.010 inches. A compression coil 56 is situated within the catheter body 12 in surrounding relation to the puller wire. The compression coil 56 extends from the proximal end of the catheter body 12 to the proximal end of the intermediate section 14. The compression coil is made of any suitable metal, preferably stainless steel, and is tightly wound on itself to provide flexibility, i.e., bending, but to resist compression. The inner diameter of the compression coil is preferably slightly larger than the diameter of the puller wire 42. The Teflon® coating on the puller wire allows it to slide freely within the compression coil. If desired, particularly if the lead wire 40 is not enclosed by the protective sheath 52, the outer surface of the compression coils can be covered by a flexible, non-conductive sheath, e.g., made of polyimide tubing, to prevent contact between the compression coils and any other wires within the catheter body 12.

As shown in FIG. 2B, the compression coil 56 is anchored at its proximal end to the proximal end of the stiffening tube 20 in the catheter body 12 by glue joint 50 and at its distal end to the intermediate section 14 by glue joint 51. Both glue joints 50 and 51 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 56 and wicks around the outer circumference to form a glue joint about the entire circumference of the compression coil.

Figure 12C:
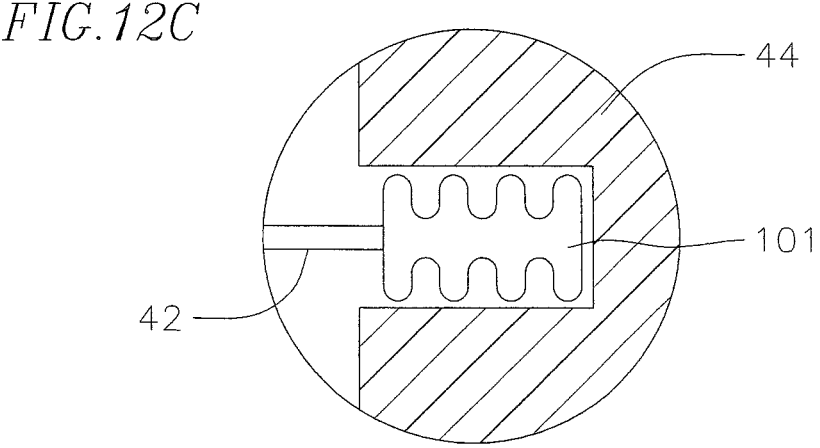
FIG. 12C is a detailed cross-sectional view of an embodiment of a distal end of a puller wire anchored in a plug of a tip electrode.

With reference to FIGS. 2B and 5, the puller wire 42 extends into the first lumen 30 of the intermediate section 14. In the illustrated embodiment of FIG. 3B, the distal end of the puller wire 42 is anchored to the distal end side wall of the first lumen 30 of the tubing 19 of the intermediate section 14. The distal end of the puller wire 42 is anchored by means of a T-bar anchor 109 created by a metal tube 120, e.g., a short segment of hypodermic stock, that is fixedly attached, e.g. by crimping, to the distal end of the puller wire 42. The tube has a section that extends a short distance beyond the distal end of the puller wire 42. A cross-piece 121 made of a small section of stainless steel ribbon or the like is soldered or welded in a transverse arrangement to the distal end of the metal tube which is flattened during the operation. A notch is created in the side wall of tubing 19 resulting in an opening in the lumen 30 carrying the puller wire 42. The cross piece 121 lies transversely within the notch. Because the length of the ribbon forming the cross-piece 121 is longer than the diameter of the opening into the lumen 30, the anchor 109 cannot be pulled completely into the lumen 30. The notch is then sealed with polyurethane glue 122 or the like to give a smooth outer surface. The glue flows into the lumen 30 to fully secure the anchor. A t-bar anchor is described in U.S. Pat. No. 6,468,260, the entire disclosure of which is hereby incorporated by reference. Other means for anchoring the distal end of the puller wire 42 would be recognized by those skilled in the art and are included within the scope of the invention. For example, another blind hole 101 (FIG. 12C) may be formed in the proximal surface of the plug 44 in which the metal tube 120 at the distal end of the puller wire may be fixed by soldering. Anchoring the puller wire 42 within the tip electrode 27 provides additional support, reducing the likelihood that the tip electrode 27 will fall off. Within the first lumen 30 of the intermediate section 14, the puller wire 42 extends through a plastic, preferably Teflon®, sheath 81, which prevents the puller wire 42 from cutting into the wall of the intermediate section 14 when the intermediate section is deflected. Longitudinal movement of the puller wire 42 relative to the catheter body 12, which results in deflection of the tip section 36, is accomplished by suitable manipulation of the control handle 16. Suitable control handles are described in U.S. Pat. No. 6,602,242, the entire disclosure of which is hereby incorporated by reference.

In the illustrated embodiment, the tip section 36 carries an electromagnetic sensor 72, and as mentioned, the electromagnetic sensor may be carried in the plastic housing 21, with its distal end anchored in the blind hole 106 in the plug 44 as shown in FIGS. 4A, 4B and 12. The electromagnetic sensor 72 is connected to an electromagnetic sensor cable 74. As shown in FIGS. 2A and 5, the sensor cable 74 extends through the third lumen 34 of the tip section 36, through the central lumen 18 of the catheter body 12, and into the control handle 16. The electromagnetic sensor cable 74 then extends out the proximal end of the control handle 16 within an umbilical cord 78 (FIG. 1) to a sensor control module 75 that houses a circuit board (not shown). Alternatively, the circuit board can be housed within the control handle 16, for example, as described in U.S. patent application Ser. No. 08/924,616, entitled "Steerable Direct Myocardial Revascularization Catheter", the disclosure of which is incorporated herein by reference. The electromagnetic sensor cable 74 comprises multiple wires encased within a plastic covered sheath. In the sensor control module 75, the wires of the electromagnetic sensor cable 74 are connected to the circuit board. The circuit board amplifies the signal received from the electromagnetic sensor 72 and transmits it to a computer in a form understandable by the computer by means of the sensor connector 77 at the proximal end of the sensor control module 75, as shown in FIG. 1. Because the catheter can be designed for single use only, the circuit board may contain an EPROM chip which shuts down the circuit board approximately 24 hours after the catheter has been used. This prevents the catheter, or at least the electromagnetic sensor, from being used twice. Suitable electromagnetic sensors for use with the present invention are described, for example, in U.S. Pat. Nos. 5,558,091, 5,443,489, 5,480,422, 5,546,951, 5,568,809, and 5,391,199 and International Publication No. WO 95/02995, the disclosures of which are incorporated herein by reference. An electromagnetic mapping sensor 72 may have a length of from about 6 mm to about 7 mm and a diameter of about 1.3 mm.

Figure 13:
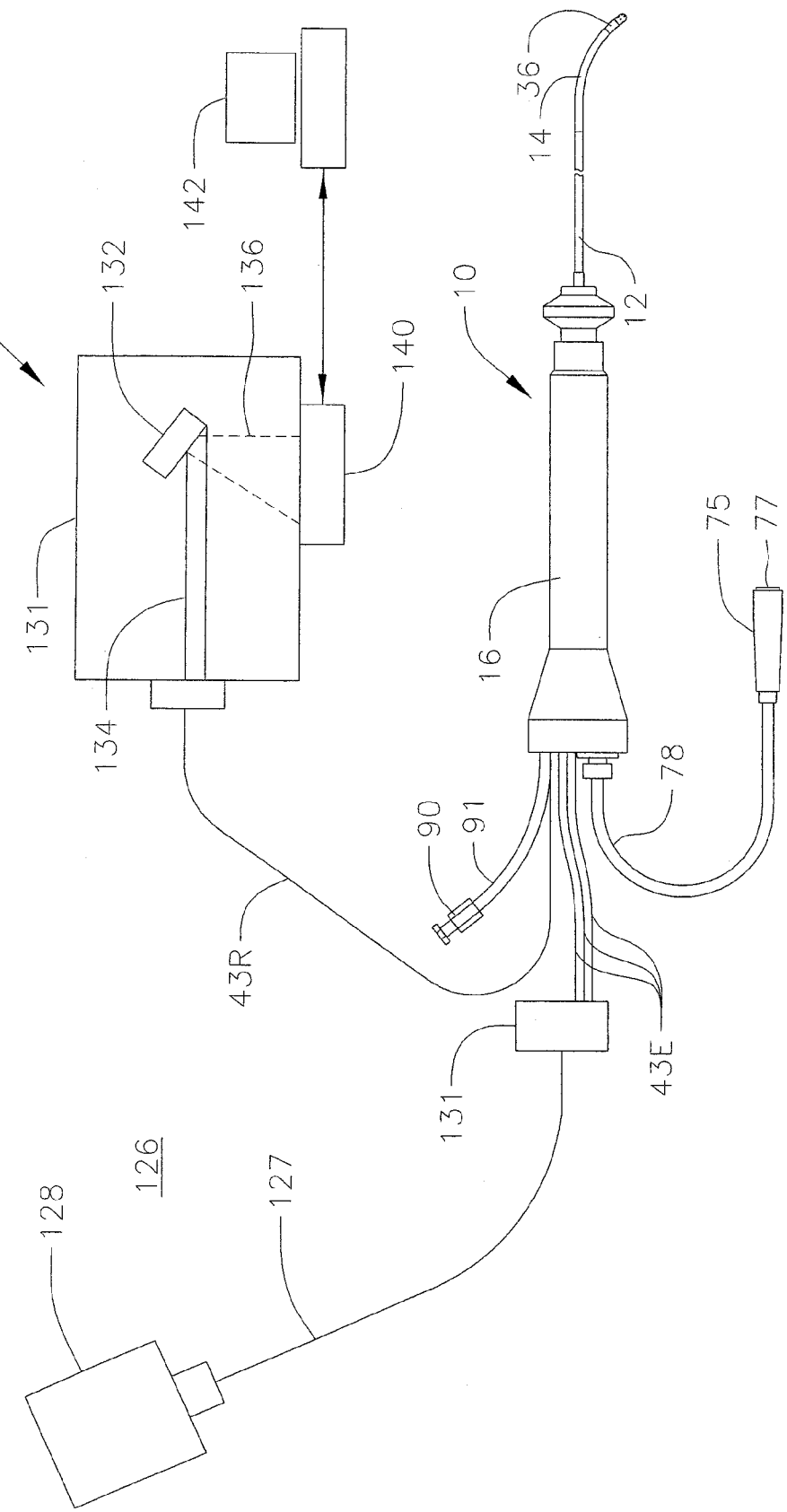
FIG. 13 is a schematic drawing showing components of an embodiment of an optical processing system for use with the catheter of the present invention.

With reference to FIG. 13, an optical processing system 126 for optically evaluating ablation tissue using the catheter 10 is illustrated. A light source 128 supplies a broadband (white; multiple wavelengths) light and/or laser light (single wavelength) radiation to the tip section 36 of the catheter 10 via cable 127 which is split by a beamsplitter 131 outputting to the emitting cables 43E. The light bearing lesion qualitative information from the tip section is transmitted by the receiving cable 43R to a detection component 130. The detection component may comprise, for example, a wavelength selective element 131 that disperses the collected light into constituent wavelengths, and a quantification apparatus 140. The at least one wavelength selective element 131 includes optics 132, as are known in the art, for example, a system of lenses, mirrors and/or prisms, for receiving incident light 134 and splitting it into desired components 136 that are transmitted into the quantification apparatus 140.

The quantification apparatus 140 translates measured light intensities into an electrical signal that can be processed with a computer 142 and displayed graphically to an operator of the catheter 10. The quantification apparatus 140 may comprise a charged coupled device (CCD) for simultaneous detection and quantification of these light intensities. Alternatively, a number of different light sensors, including photodiodes, photomultipliers or complementary metal oxide semiconductor (CMOS) detectors may be used in place of the CCD converter. Information is transmitted from the quantification device 140 to the computer 142 where a graphical display or other information is generated regarding parameters of the lesion. A suitable system for use with the catheter 10 is described in U.S. application Ser. No. 11/281,179 and Ser. No. 11/281,853, the entire disclosures of which are hereby incorporated by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. In that regard, the tip electrode may be configured with illumination and/or collection openings without regard to the configuration or location of the various sections of the tip electrode. Moreover, the tip electrode may be modified such that any type and number of openings can be placed anywhere on the tip electrode. For example, there could be multiple openings on the most distal section of the tip dome instead of a single opening, or there could be an illumination opening instead of a receiving opening. In addition, the openings can be of any shape, and are only limited by manufacturing methods available, such as laser drilling, photo-chemical etching, EDM machining, etc.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising:
   a catheter body;
   a tip electrode distal the catheter body, the tip electrode having a shell wall, a hollow cavity and a plug, the shell wall having at least an illumination opening and a collection opening, and the plug sealing the hollow cavity at a proximal end of the shell wall;
   a first fiber optic cable in communication with the illumination opening;
   a second fiber optic cable in communication with the hollow cavity; and
   an irrigation tubing configured to deliver irrigation fluid to the hollow cavity;
   wherein light emitted from the first fiber optic cable exits the tip electrode to reach tissue through the illumination opening in defining a first path and returns to the tip electrode from the tissue through the collection opening into the hollow cavity where the light is first collected and thereafter received by the second fiber optic cable in defining a second path, the first and second paths being optically isolated from each other within the tip electrode; and
   wherein the first and second fiber optic cables and the irrigation tubing extend in passages in the plug.

2. A catheter of claim 1, wherein the irrigation tubing is anchored in its passage in the plug.

3. A catheter of claim 1, wherein the first path includes (a) passage through the first fiber optic cable and (b) exit to outside the tip electrode through the illumination opening, and wherein the second path includes (a) passage through the collection opening, (b) collection in the hollow cavity, and (c) passage through the second fiber optic cable.

4. A catheter of claim 1, wherein the first fiber optic cable extends through the hollow cavity and is optically isolated from the hollow cavity.

5. A catheter of claim 4, wherein the first fiber optic cable is optically isolated by a coating of reflective buffer material thereon.

6. A catheter of claim 1, wherein the illumination opening has a semi-spherical cross section.

7. A catheter of claim 1, wherein the illumination opening is filled with an optically scattering material.

8. A catheter of claim 1, wherein the shell has a longitudinal axis and first, second and third sections, the first section being generally perpendicular to the longitudinal axis, the second section being generally at an angle between about zero and 90 degrees to the longitudinal axis, and the third section being generally parallel to the longitudinal axis.

9. A catheter of claim 8, wherein the first section has the collection opening and the second section has the illumination opening and the third section has another collection opening.

10. A catheter of claim 8, wherein the first section is distal of the second section which is distal of the third section.

11. A catheter of claim 8, wherein the first section has the collection opening, and the second section has the illumination opening.

12. A catheter of claim 8, wherein the second section has multiple illumination openings, and the third section has multiple collection openings, and wherein the openings within each section are equi-angular from each other about the longitudinal axis.

13. A catheter of claim 8, wherein the angle of the second section is about 45 degrees.

14. A catheter of claim 8, wherein the angle of the second section is about 30 to about 60 degrees.

15. A catheter of claim 1, wherein the hollow cavity includes a distal dome cavity.

16. A catheter of claim 1, wherein the first and second fiber optic cables are fixed to the plug within their respective passages.

17. A catheter of claim 1, wherein the tip electrode is adapted for RF ablation.

18. A catheter of claim 17, further comprising an electrode lead wire attached at its distal end within a blind hole in the plug.

19. A catheter of claim 1, further comprising a deflectable intermediate section between the catheter body and the tip electrode.

20. A catheter of claim 1, further comprising a temperature sensor.

21. A catheter of claim 20, wherein the temperature sensor is located within a blind hole in the plug.

22. A catheter of claim 1, further comprising a location sensor.

23. A catheter according to claim 22, wherein the location sensor is located within a blind hole in the plug.

24. A catheter, comprising:
   a catheter body;
   a tip electrode distal the catheter body, the tip electrode having a shell wall, a hollow cavity and a plug, the shell wall having illumination openings and collection openings, and the plug sealing the hollow cavity at a proximal end of the shell wall;
   at least one emitting fiber optic cable in communication with at least one of the illumination openings;
   at least one receiving fiber optic cable in communication with the hollow cavity; and
   an irrigation tubing configured to deliver irrigation fluid to the hollow cavity;
   wherein light emitted from the at least one emitting fiber optic cable exits the tip electrode to reach tissue through the at least one of the illumination openings in defining a first path and returns to the tip electrode from the tissue through at least one of the collection openings into the hollow cavity where the light is first collected and thereafter received by the at least one receiving fiber optic cable in defining a second path, the first and second paths being optically isolated from each other within the tip electrode; and wherein the at least one emitting fiber optic cable, the at least one receiving fiber optic cable, and the irrigation tubing extend in passages in the plug.

25. A catheter of claim 24, wherein a distal end of the at least one emitting fiber optic cable extends substantially into the at least one of the illumination openings.

26. A catheter of claim 24, wherein the at least one receiving fiber optic cable is configured to receive light in the hollow cavity.

27. A catheter of claim 24, wherein at least one of the collection openings is at a distal end of the tip electrode along a longitudinal axis of the tip electrode.

28. A catheter of claim 24, wherein the at least one emitting fiber optic cable comprises a respective emitting fiber optic cable for each of the illumination openings.

29. A catheter of claim 24, wherein the tip electrode is configured with at least four collection openings and three illumination openings.

30. A catheter of claim 24, wherein the irrigation tubing is anchored in its passage in the plug.

31. A catheter of claim 24, wherein the at least one emitting fiber optic cable extends through the hollow cavity and is optically isolated from the hollow cavity.

32. A catheter of claim 31, wherein the at least one emitting fiber optic cable is optically isolated by a coating of reflective buffer material thereon.

33. A catheter of claim 24, wherein the shell has a longitudinal axis and first, second and third sections, the first section being generally perpendicular to the longitudinal axis, the second section being generally at an angle between about zero and 90 degrees to the longitudinal axis, and the third section being generally parallel to the longitudinal axis.

34. A catheter of claim 33, wherein the first section and the third section have the collection openings and the second section has the illumination openings.

35. A catheter of claim 24, further comprising a deflectable intermediate section between the catheter body and the tip electrode.

36. A catheter of claim 24, wherein the tip electrode is configured for ablation, and the catheter further comprises an electrode lead wire attached at its distal end within a blind hole in the plug.

* * * * *